US010365168B2

(12) United States Patent
Ban

(10) Patent No.: US 10,365,168 B2
(45) Date of Patent: Jul. 30, 2019

(54) ELECTRONIC DEVICE AND METHOD FOR DETERMINING TEMPERATURE IN THE ELECTRONIC DEVICE

(71) Applicant: Samsung Electronics Co., Ltd., Gyeonggi-do (KR)

(72) Inventor: Young-Kyun Ban, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 389 days.

(21) Appl. No.: 15/190,918

(22) Filed: Jun. 23, 2016

(65) Prior Publication Data

US 2016/0377491 A1 Dec. 29, 2016

(30) Foreign Application Priority Data

Jun. 23, 2015 (KR) ........................ 10-2015-0089274

(51) Int. Cl.

*G01K 13/00* (2006.01)
*G01K 1/20* (2006.01)
*G06F 1/16* (2006.01)
*A61B 5/15* (2006.01)

(52) U.S. Cl.

CPC ............ *G01K 13/002* (2013.01); *G01K 1/20* (2013.01); *A61B 5/150954* (2013.01); *A61B 2562/0271* (2013.01); *G06F 1/163* (2013.01)

(58) Field of Classification Search

CPC ....... A61B 5/01; A61B 5/150954; A61B 5/68; A61B 2562/0271; G06F 1/163
See application file for complete search history.

(56) References Cited

U.S. PATENT DOCUMENTS 4,509,531 A * 4/1985 Ward ........................ A61B 5/01 374/142
2005/0001596 A1* 1/2005 Lovett ...................... G01K 1/02 320/150
2010/0100004 A1 4/2010 van Someren
2016/0038055 A1* 2/2016 Wheeler ............. A61B 5/0533 600/547

* cited by examiner

*Primary Examiner* — Daniel S Larkin
*Assistant Examiner* — Anthony W Megna Fuentes
(74) *Attorney, Agent, or Firm* — The Farrell Law Firm, P.C.

(57) ABSTRACT

An electronic device detachable from and attachable to a user and a method of determining a temperature in the electronic device are provided. The electronic device includes a housing, a battery mounted in the housing, a coupling member connected to a part of the housing and configured to detachably couple the electronic device to a part of the user's body, a conductive member disposed on one surface of the housing or on one surface of the coupling member and exposed externally, in electrical connection to the battery, a temperature sensor electrically connected to the conductive member, and a circuit electrically connected to the battery, the conductive member, and the temperature sensor, wherein the circuit is configured to monitor a value of a current or a voltage received through the conductive member, and to charge the battery using the current or operate the temperature sensor, based on at least a part of the monitored value.

4 Claims, 15 Drawing Sheets

START
DETERMINE WHETHER EXTERNAL DEVICE CONNECTOR HAS BEEN CONNECTED TO EXTERNAL DEVICE — 402
404 EXTERNAL DEVICE CONNECTED? YES / NO
DETERMINE WHETHER CONTACT CONTACTS SKIN — 406
408 SKIN CONTACTED? YES / NO
DETERMINE SKIN TEMPERATURE BY TEMPERATURE SENSOR CONNECTED TO EXTERNAL DEVICE CONNECTOR — 410
EXECUTE FUNCTION BY EXTERNAL DEVICE — 412
414 CHARGING FUNCTION EXECUTED? YES / NO
DETERMINE CHARGING TEMPERATURE BY TEMPERATURE SENSOR CONNECTED TO EXTERNAL DEVICE CONNECTOR — 416
END

ELECTRONIC DEVICE AND METHOD FOR DETERMINING TEMPERATURE IN THE ELECTRONIC DEVICE

PRIORITY

This application claims priority under 35 U.S.C. § 119(a) to a Korean Patent Application filed on Jun. 23, 2015 in the Korean Intellectual Property Office and assigned Serial No. 10-2015-0089274, the entire disclosure of which is incorporated herein by reference.

BACKGROUND

1. Field of the Disclosure

The present disclosure relates generally to an electronic device and a method for determining temperature in the electronic device, and more particularly, to an electronic device for and a method of measuring skin temperature through an external device connector provided in the electronic device without an additional electrode.

2. Description of the Related Art

In general, an electronic device is a device that executes a certain function according to a program loaded in the device, such as a home appliance, an electronic note, a Portable Multimedia Player (PMP), a mobile communication terminal, a tablet Personal Computer (PC), a video/audio player, a desktop/laptop computer, and an in-vehicle navigator. For example, these electronic devices can output stored information visually or audibly. As the integration level of electronic devices has increased and ultra high-speed, large-capacity wireless communication has become widespread, various functions have been installed in a single mobile communication terminal.

For example, an entertainment function such as gaming, a multimedia function such as a music/video player, a communication and security function such as mobile banking, a scheduling function, and an electronic wallet function as well as a communication function are integrated into one electronic device.

For example, an electronic device may be connected to at least one other electronic device by wired/wireless communication and the connected electronic devices may execute a function by interacting with each other. As electronic devices are equipped with various types of sensors, many services are provided through the electronic devices using sensed information.

According to the current state of the art, for example, an electronic device wearable on a part of the body (hereinafter, referred to as a wearable device) should be equipped with electrodes that contact the body in order to measure skin temperature.

If an additional structure (for example, electrodes exposed externally from a case) is provided in a wearable device to measure skin temperature, product design should be further considered and there may exist design difficulty in adding the additional structure or part.

In addition, if skin temperature is measured by a temperature sensor in an electronic device, the measured skin temperature may be erroneous because it is affected by the ambient temperature of the electronic device.

Furthermore, when an electronic device measures its ambient temperature, the temperature sensor internal to the electronic device is affected by heat emission in the electronic device, which may make it difficult to measure an accurate ambient temperature.

SUMMARY

An aspect of the present disclosure is to provide an electronic device for measuring skin temperature accurately and readily through an external device connector provided in the electronic device without the need for an additional electrode configured for measuring skin temperature, when the skin temperature is to be measured, and a method for determining temperature in the electronic device.

Another aspect of the present disclosure is to provide an electronic device for measuring ambient temperature accurately through a temperature sensor connected to an antenna, and a method for determining temperature in the electronic device.

In accordance with an aspect of the present disclosure, there is provided an electronic device detachable from and attachable to a user. The electronic device includes a housing, a battery mounted in the housing, a coupling member connected to a part of the housing and configured to detachably couple the electronic device to a part of the user's body, a conductive member disposed on one surface of the housing or on one surface of the coupling member and exposed externally, in electrical connection to the battery, a temperature sensor electrically connected to the conductive member, and a circuit electrically connected to the battery, the conductive member, and the temperature sensor, wherein the circuit is configured to monitor a value of a current or a voltage received through the conductive member, and to charge the battery using the current or operate the temperature sensor, based on at least a part of the monitored value.

In accordance with another aspect of the present disclosure, there is provided an electronic device detachable from and attachable to a user. The electronic device includes a housing, a battery mounted in the housing, a coupling member connected to a part of the housing and configured to detachably couple the electronic device to a part of the user's body, a contact exposed on one surface of the housing or on one surface of the coupling member and electrically connected to the battery, a temperature sensor electrically connected to the contact, and a circuit electrically connected to the battery, the contact, and the temperature sensor, wherein the circuit is configured to receive a current generated by an external material through contact between the external material and the contact, charge the battery using the current based on a determination made based on the current that a voltage applied to at least a part of the circuit is greater than or equal to a threshold, and sense a temperature of the external material through the temperature sensor based on a determination that the voltage is less than the threshold.

In accordance with another aspect of the present disclosure, there is provided an electronic device detachable from and attachable to a user. The electronic device includes a housing, an external device connector including at least one contact exposed externally from the housing and electrically connected to an external electronic device, a conductive connection member connected to the at least one contact of the external device connector, and a first temperature sensor connected to the conductive connection member and configured to sense a temperature.

In accordance with another aspect of the present disclosure, there is provided a method of determining a temperature in an electronic device. The method includes determining whether an external device is connected to an external device connector including at least one contact exposed externally from a housing of the electronic device and electrically connected to the external electronic device, sensing the temperature by a first temperature sensor connected to the at least one contact of the external device connector, and determining the temperature sensed by the first temperature sensor to be a skin temperature of a user wearing the electronic device, if it is determined that the external electronic device is not connected to the external device connector.

BRIEF DESCRIPTION OF THE DRAWINGS

The above and other aspects, features and advantages of certain embodiments of the present disclosure will be more apparent from the following description, taken in conjunction with the accompanying drawings, in which.

DETAILED DESCRIPTION OF EMBODIMENTS OF THE PRESENT DISCLOSURE

Figure 1:
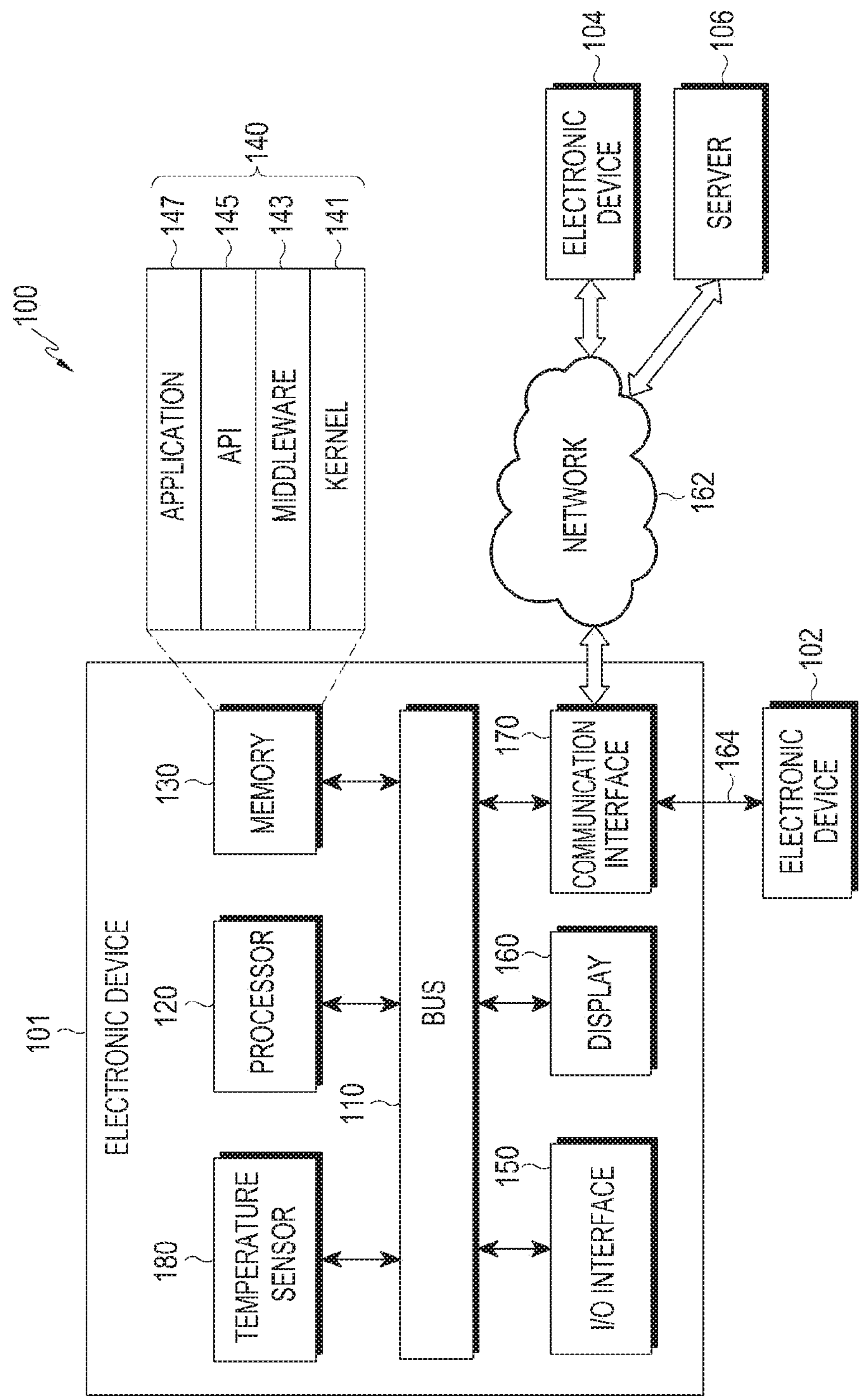
FIG. 1 is a block diagram of a network environment according to an embodiment of the present disclosure.

Various embodiments of the present disclosure are described with reference to the accompanying drawings. However, the scope of the present disclosure is not intended to be limited to the embodiments disclosed in the present disclosure and it is to be understood that the present disclosure covers all modifications, equivalents, and/or alternatives falling within the scope of the present disclosure as defined by the appended claims and their equivalents. In the descriptions below of the accompanying drawings, like reference numerals denote the same components.

In the present disclosure, the terms "have," "may have," "include," and "may include" signify the presence of a certain feature (for example, a number, a function, an operation, or a component like a part), but do not signify excluding the presence of an additional feature.

In the present disclosure, the terms "A or B," "at least one of A and/or B," and "one or more of A and/or B" may cover all possible combinations of enumerated items. For example, "A or B," "at least one of A and B," or "at least one of A or B" may represent all of the cases of (1) inclusion of at least one A, (2) inclusion of at least one B, and (3) at least one A and at least one B.

The terms, as used in an embodiment of the present disclosure, "first" and "second" may modify the names of various components irrespective of sequence and/or importance, but do not limit the components. These expressions may be used to distinguish one component from another component. For example, a first User Equipment (UE) and a second UE may indicate different UEs irrespective of sequence or importance. For example, a first component may be referred to as a second component and vice versa without departing from the scope and spirit of the present disclosure.

When it is indicated that a component (for example, a first component) is "operatively or communicatively coupled with/to" or "connected to" another component (for example, a second component), it should be understood that the component is connected to the other component directly or through another component (for example, a third component). In contrast, when it is indicated that a component (for example, a first component) is "directly connected" or "directly coupled" to another component (for example, a second component), it may be understood that there is no other component (for example, a third component) between the components.

The term "configured to" as used herein may be replaced with, for example, the term "suitable for," "having the capacity to," "designed to," "adapted to," "made to," or "capable of" under certain circumstances. The term "configured to" may not necessarily indicate "specifically designed to" in hardware. Instead, the term "configured to" may indicate that a device may be "capable of" something with another device or part. For example, "a processor configured to execute A, B, and C" may indicate a dedicated processor (for example, an embedded processor) for performing the corresponding operations or a general-purpose processor (for example, a Central Processing Unit (CPU) or an application processor) for performing the corresponding operations.

The terms as used in the present disclosure are provided merely to describe certain embodiments of the present disclosure, and are not intended to limit the scope of the present disclosure. It is to be understood that singular forms include plural referents unless the context clearly dictates otherwise. The terms used in the following description and claims may have the same meanings as generally understood by those skilled in the art. The terms as generally defined in dictionaries may be interpreted as having the same or similar meanings as contextual meanings of related technology. Unless otherwise defined, the terms should not be interpreted as having ideally or excessively formal meanings.

When needed, even the terms as defined in the present disclosure may not be interpreted as excluding an embodiment of the present disclosure.

According to an embodiment of the present disclosure, an electronic device may be at least one of, for example, a smartphone, a tablet PC, a mobile phone, a video phone, an electronic book (e-book) reader, a desktop PC, a laptop PC, a netbook computer, a workstation, a server, a Personal Digital Assistant (PDA), a PMP, a Moving Picture Experts Group (MPEG-1) audio layer-3 (MP3) player, a mobile medical equipment, a camera, and a wearable device (for example, smart glasses, a Head-Mounted Device (HMD), electronic clothes, an electronic bracelet, an electronic necklace, an electronic appcessory, an electronic tattoo, a smart mirror, or a smart watch).

According to an embodiment of the present disclosure, an electronic device may be a smart home appliance. For example, the smart home appliance may be at least one of a Television (TV), a Digital Versatile Disk (DVD) player, an audio player, a refrigerator, an air conditioner, a vacuum cleaner, an oven, a microwave oven, a washing machine, an air purifier, a set-top box, a home automation control panel, a security control panel, a TV box (for example, Samsung HomeSync™, Apple TV™, Google TV™, or the like), a game console (for example, Xbox™, PlayStation™, or the like), an electronic dictionary, an electronic key, a camcorder, and an electronic picture frame.

According to an embodiment of the present disclosure, an electronic device may be at least one of a medical device (for example, a portable medical meter such as a blood glucose meter, a heart rate meter, a blood pressure meter, or a thermometer, a Magnetic Resonance Angiography (MRA) device, a Magnetic Resonance Imaging (MRI) device, a Computed Tomography (CT) device, an imaging device, an ultrasonic device, or the like), a navigation device, a Global Positioning System (GPS) receiver, an Event Data Recorder (EDR), a Flight Data Recorder (FDR), an automotive infotainment device, a naval electronic device (for example, a naval navigation device, a gyrocompass, or the like), an avionic electronic device, a security device, an in-vehicle head unit, an industrial or consumer robot, an Automated Teller Machine (ATM) in a financial facility, a Point Of Sales (POS) device in a shop, an Internet of Things (IoT) device (for example, a light bulb, various sensors, an electricity or gas meter, a sprinkler, a fire alarm, a thermostat, a street lamp, a toaster, sporting goods, a hot water tank, a heater, or a boiler), and the like.

According to an embodiment of the present disclosure, an electronic device may be at least one of furniture, part of a building/structure, an electronic board, an electronic signature receiving device, a projector, and various measuring devices (for example, water, electricity, gas or electromagnetic wave measuring devices). An electronic device according to an embodiment of the present disclosure may be one or a combination of two or more of the foregoing devices. Also, an electronic device according to an embodiment of the present disclosure may be a flexible device. In addition, it will be apparent to one having ordinary skill in the art that an electronic device according to the present disclosure is not limited to the foregoing devices and includes an electronic device produced as technology develops.

With reference to the attached drawings, an electronic device according to an embodiment of the present disclosure is described below. In the present disclosure, the term "user" may refer to a person or device (for example, an artificial intelligence electronic device) that uses an electronic device.

FIG. 1, is a block diagram of a network environment 100 according to an embodiment of the present disclosure.

Referring to FIG. 1, the network environment 100 includes an electronic device 101. The electronic device 101 may include at least one of a bus 110, a processor 120, a memory 130, an Input/Output (I/O) interface 150, a display 160, a communication interface 170, or a temperature sensor 180. In an embodiment of the present disclosure, at least one of the components may be omitted in, or a component may be added to, the electronic device 101.

The bus 110 may include a circuit that interconnects, for example, the foregoing components 110 to 180 and allow communication (for example, control messages and/or data transfers) between the foregoing components 110 to 180.

The processor 120 may include one or more of a CPU, an Application Processor (AP), and a Communication Processor (CP). The processor 120 may, for example, execute a computation or process data related to control and/or communication of at least one other component of the electronic device 101.

The memory 130 may include a volatile memory and/or a non-volatile memory. The memory 130 may, for example, store instructions or data related to at least one other component. For example, the memory 130 may store software and/or programs 140. The programs 140 may include, for example, a kernel 141, middleware 143, an Application Programming Interface (API) 145, and/or at least one application program (or application) 147. At least a part of the kernel 141, the middleware 143, or the API 145 may be called an Operating System (OS).

The kernel 141 may control or manage system resources (for example, the bus 110, the processor 120, or the memory 130) that are used in executing operations or functions implemented in other programs such as the middleware 143, the API 145, or the at least one application program 147. Also, the kernel 141 may provide an interface for allowing the middleware 143, the API 145, or the at least one application program 147 to access and control or manage individual components of the electronic device 101.

The middleware 143 may serve as a medium through which the kernel 141 may communicate with the API 145 or the at least one application program 147 to transmit and receive data. In addition, the middleware 143 may perform control operations (for example, scheduling or load balancing) in regard to work requests by at least one application program 147 by, for example, assigning priorities for using system resources (e.g., the bus 110, the processor 120, or the memory 130) of the electronic device 101 with the at least one application program 147.

The API 145 is an interface that may control functions that the at least one application program 147 provides at the kernel 141 or the middleware 143. For example, the API 145 may include at least one interface or function (for example, a command) for file control, window control, video processing, or text control.

The I/O interface 150 may act as an interface that provides a command or data received from a user or an external device to the other component(s). Further, the I/O interface 150 may output a command or data received from the other component(s) to the user or the external device. According to an embodiment of the present disclosure, the I/O interface 150 may include at least one external device connector connected electrically to an external electronic device. The external device connector may include at least one contact that is exposed externally from a housing of the electronic device 101 and electrically connected to the external electronic device.

According to an embodiment of the present disclosure, the display 160 may display information about measured or determined skin temperature, corrected skin temperature, or ambient temperature of the electronic device 101. For example, the display 160 may include a Liquid Crystal Display (LCD), a Light Emitting Diode (LED) display, an Organic LED (OLED) display, a Microelectromechanical Systems (MEMS) display, or an electronic paper display. The display 160 may display, for example, various types of content (for example, text, an image, a video, an icon, or a symbol) to the user. The display 160 may include a touch screen and receive, for example, a touch input, a gesture input, a proximity input, or a hovering input through an electronic pen or a part of a user's body.

The communication interface 170 may establish communication between the electronic device 101 and an external device (for example, a first electronic device 102, a second electronic device 104, or a server 106). For example, the communication interface 170 may be connected to a network 162 by wireless or wired communication and communicate with the second electronic device 104 or the server 106 over the network 162. The communication interface 170 may communicate directly with the first electronic device 102, for example, wirelessly or wiredly, as indicated by reference numeral 164.

The wireless communication may be conducted using, for example, at least one of Long Term Evolution (LTE), LTE-Advanced (LTE-A), Code Division Multiple Access (CDMA), Wideband CDMA (WCDMA), Universal Mobile Telecommunication System (UMTS), Wireless Broadband (WiBro), or Global System for Mobile communications (GSM)), as a cellular communication protocol. The wired communication may be conducted in conformance to, for example, at least one of a Universal Serial Bus (USB), a High Definition Multimedia Interface (HDMI), a Recommended Standard 232 (RS-232), or a Plain Old Telephone Service (POTS). The network 162 may be a communication network, for example, at least one of a computer network (for example, a Local Area Network (LAN) or a Wide Area Network (WAN)), the Internet, or a telephone network.

Each of the first and second external electronic devices 102 and 104 may be of the same type as, or a different type from, the electronic device 101. According to an embodiment of the present disclosure, the server 106 may include a group of one or more servers. According to an embodiment of the present disclosure, all or a part of the operations performed in the electronic device 101 may be performed in one or more of the electronic devices 102 and 104 or the server 106. According to an embodiment of the present disclosure, if the electronic device 101 is to perform a function or a service automatically or upon request, the electronic device 101 may request at least a part of the functions related to the function or the service from the electronic device 102 or 104 or the server 106, instead of performing the function or the service autonomously, or additionally. The electronic device 102 or 104 or the server 106 may execute the requested function or an additional function and provide a result of the function execution to the electronic device 101. The electronic device 101 may provide the requested function or service using the received result or by additionally processing the received result. For this purpose, for example, cloud computing, distributed computing, or client-server computing may be used.

While the electronic device 101 is shown in FIG. 1 as having the communication interface 170 and communicating with the external electronic device 104 or the server 106 through the network 162, the electronic device 101 may be configured to independently operate without any separate communication function according to an embodiment of the present disclosure.

According to an embodiment of the present disclosure, the server 106 may support an operation of the electronic device 101 by performing at least one of the operations (or functions) implemented in the electronic device 101. For example, the server 106 may include a temperature determination server module that may support the processor 120 of the electronic device 101. For example, the temperature determination server module may include at least one component of the processor 120 and thus may perform (or take over) at least one of the operations (or functions) implemented by the processor 120.

The temperature sensor 180 may use at least a part of information acquired from other components (for example, the processor 120, the memory 130, the I/O interface 150, or the communication interface 170) and provide the at least partial information to the user in various manners. According to an embodiment of the present disclosure, the temperature sensor 180 may also sense skin temperature through the external device connector and transmit the sensing result to the processor 120. Further, the temperature sensor 180 may operate under the control of the processor 120.

For example, the temperature sensor 180 may sense skin temperature according to whether the I/O interface 150 (for example, the external device connector) is connected to an external electronic device according to an embodiment of the present disclosure. For example, the processor 120 may control an operation of the temperature sensor 180 or determine a sensing result of the temperature sensor 180 to be skin temperature by determining whether the I/O interface 150 (for example, the external device connector) is connected to an external electronic device. The I/O interface 150, the temperature sensor 180, and the processor 120 according to an embodiment of the present disclosure are described below.

While the temperature sensor 180 is shown in FIG. 1 as a module configured separately from the processor 120, at least a part of the temperature sensor 180 may be included in the processor 120 or at least one other module.

With reference to FIGS. 2 to 15, detailed configurations of electronic devices and methods for determining temperature in the electronic devices according to an embodiment of the present disclosure are described below.

Figure 2:
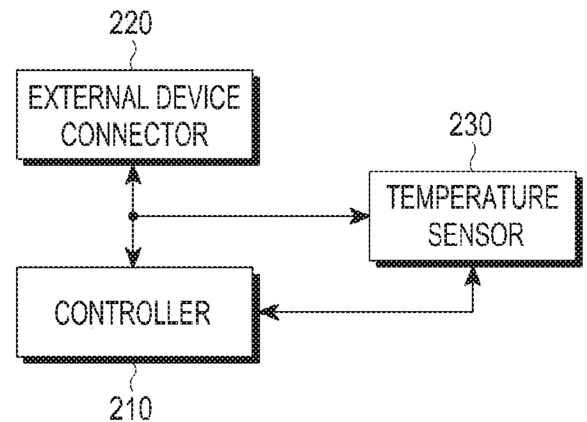
FIG. 2 is a block diagram of an electronic device according to an embodiment of the present disclosure.

FIG. 2 is a block diagram of an electronic device according to an embodiment of the present disclosure.

Referring to FIG. 2, the electronic device according to an embodiment of the present disclosure may include at least one of a controller 210, an external device connector 220, and a temperature sensor 230.

All or part of a function of each component in the electronic device illustrated in FIG. 2 may be included in at least one component illustrated in FIG. 1. For example, at least a part of the controller 210 may be included in the processor 120 of FIG. 1. Also, at least a part of the external device connector 220 may be included in the I/O interface 150 or the communication interface 170 illustrated in FIG. 1. The external device connector 220 may be connected electrically to the controller 210 or the temperature sensor 230.

According to an embodiment of the present disclosure, the electronic device may be electrically connected to a second electronic device through the external device connector 220. According to an embodiment of the present disclosure, the second electronic device may be referred to as an "external electronic device" for the electronic device.

The external device connector 220 may be provided with at least one contact. As a contact point (for example, a Pogo pin) in a connector of the electronic device, or a connection cable to be connected to the eternal electronic device contacts each contact of the external device connector 220, the electronic device may be electrically connected to the external electronic device. For example, the external electronic device may be a charger for charging the electronic device or an electronic device or storage medium that conducts data communication with the electronic device.

If the electronic device is electrically connected to the external electronic device through the external device connector 220, the electronic device may transmit data or power to the external electronic device or receive data or power from the external electronic device. At least a part of the external device connector 220 may be included in the I/O interface 150 illustrated in FIG. 1.

The controller 210 may control the electronic device to communicate with the external electronic device through the external device connector 220 and may process data received from the external electronic device. At least a part of the functions of the controller 210 may be included in the processor 120 illustrated in FIG. 1.

According to an embodiment of the present disclosure, the temperature sensor 230 may be connected to the external device connector 220 directly or indirectly. For example, the external device connector 220 and the temperature sensor 230 may be connected to each other by direct contact or by a conductive material. For example, the temperature sensor 230 may be connected to at least one contact included in the external device connector 220 directly or indirectly.

The temperature sensor 230 may sense the temperature of the external device connector 220 through a connection to the external device connector 220. For example, if the electronic device is a wearable device and a user wears the electronic device, at least one contact of the external device connector 220 contacts the skin of the user, and the temperature sensor 230 may measure the skin temperature of the user through the external device connector 220. Information related to the temperature measured by the temperature sensor 230 may be transmitted to the controller 210.

The controller 210 may receive the information related to the measured temperature from the temperature sensor 230 and may subject the received information to various processes. In addition, the controller 210 may control an operation of the temperature sensor 230. The controller 210 may control an operation of the temperature sensor 230 or use the information related to the temperature received from the temperature sensor 230 according to a connection state between the external device connector 220 and the external electronic device.

According to an embodiment of the present disclosure, if the controller 210 determines that there is no external connection to the external device connector 220 or the external device connector 220 contacts the skin of the user, the controller 210 may determine the temperature measured by the temperature sensor 230 to be the skin temperature of the user. According to an embodiment of the present disclosure, when the controller 210 is to measure skin temperature through the temperature sensor 230, the controller 210 may control the shut-off of a circuit connected from the external device connector 220 to other structures of the electronic device (for example, a battery or a rechargeable battery) in order to determine an accurate skin temperature.

According to an embodiment of the present disclosure, the controller 210 may determine whether the external electronic device has been connected or the type of the external electronic device through an IDentification (ID) pin among a plurality of contacts provided in the external device connector 220.

According to an embodiment of the present disclosure, the controller 210 may measure a voltage of the ID pin of the external device connector 220 and determine a connection state of the external device connector 220 by comparing the measured voltage with a predetermined voltage.

The controller 210 may display, on a screen, information related to the external electronic device connected through the external device connector 220, charged state information if a charger as an exemplary external electronic device is connected, or information related to temperature measured by the temperature sensor 230.

Figure 3:
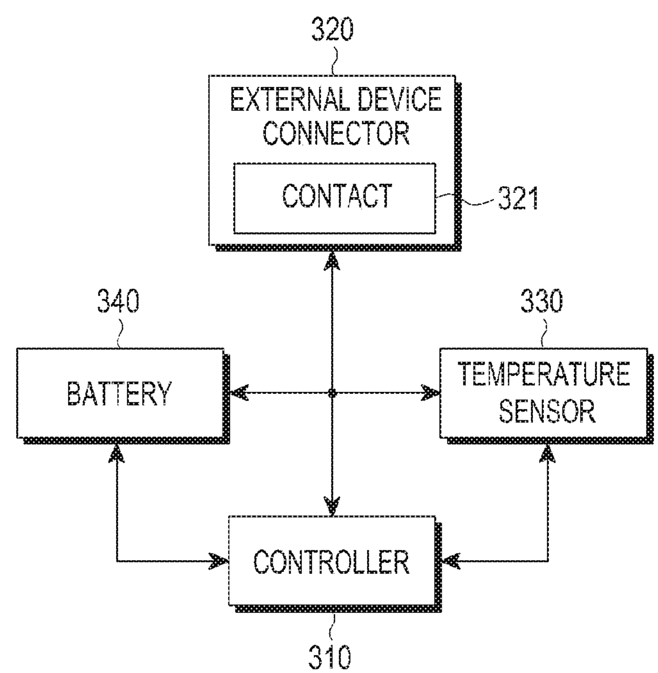
FIG. 3 is a block diagram of an electronic device according to an embodiment of the present disclosure.

FIG. 3 is a block diagram of an electronic device according to an embodiment of the present disclosure.

Referring to FIG. 3, the electronic device according to an embodiment of the present disclosure may include at least one of a controller 310, an external device connector 320, a temperature sensor 330, and a battery 340.

All or part of a function of each component in the electronic device illustrated in FIG. 3 may be included in at least one component illustrated in FIG. 1. For example, at least a part of the controller 310 may be included in the processor 120 of FIG. 1. In addition, at least a part of the external device connector 320 may be included in the I/O interface 150 or the communication interface 170 illustrated in FIG. 1. The external device connector 320 may be connected electrically to the controller 310 or the temperature sensor 330.

According to an embodiment of the present disclosure, the electronic device may be electrically connected to a second electronic device through the external device connector 320. At least a part of the controller 310, the external device connector 320, or the temperature sensor 330 illustrated in FIG. 3 may execute the same function as the controller 210, the external device connector 220, or the temperature sensor 230 illustrated in FIG. 2. The following description is given of FIG. 3, with a description of the same functions described in FIG. 2 omitted.

According to an embodiment of the present disclosure, at least one of a plurality of contacts 321 included in the external device connector 320 may be connected to the battery 340. For example, if a charger is connected to the external device connector 320, for charging the electronic device, power supplied from the charger is transferred to the battery 340, thus charging the battery 340.

According to an embodiment of the present disclosure, if the controller 310 determines that the charger has been connected to the external device connector 320 or a voltage greater than or equal to a predetermined voltage is applied through the external device connector 320, the controller 310 may determine that the charger has been connected. According to an embodiment of the present disclosure, if the battery 340 is being charged through the external device connector 320, the temperature measured through the temperature sensor 330 may be determined to not be a skin temperature but a charging temperature. For example, if a charging temperature is determined through the temperature sensor 330 during charging, information related to the temperature measured by the temperature sensor 330 may be used as information for preventing over-temperature of the battery 340.

According to an embodiment of the present disclosure, if the battery 340 is being charged through the external device connector 320, the temperature sensor 330 may be configured to be disconnected from the external device connector 320.

According to an embodiment of the present disclosure, each function unit or module may indicate a function or structural coupling between hardware for realizing the an embodiment of the present disclosure and software for driving the hardware. For example, each function unit or module may refer to a predetermined code and a logical unit of hardware resources for executing the code. Those skilled in the art can readily understand that the function unit or module does not necessarily indicate a physically connected code or one type of hardware.

According to an embodiment of the present disclosure, an electronic device detachably wearable on a user includes a housing, a battery mounted in the housing, a coupling member configured to detachably couple the electronic device to a part of the body of the user, a conductive member that is disposed on one surface of the housing or the coupling member, which is exposed externally in an electrical connection to the battery, a temperature sensor electrically connected to the conductive member, and a circuit electrically connected to the battery, the conductive member, and the temperature sensor. The circuit may be configured to monitor the intensity of a current or a voltage received through the conductive member, and charge the battery using the current or operate the temperature sensor based on at least a part of the monitored value.

According to an embodiment of the present disclosure, the electronic device may further include a conductive member electrically connected to the temperature sensor and the circuit.

According to an embodiment of the present disclosure, the circuit may be configured to correct temperature sensed by the temperature sensor based on the ambient temperature of the electronic device sensed through the conductive member.

According to an embodiment of the present disclosure, an electronic device detachably wearable by a user includes a housing, a battery mounted in the housing, a coupling member configured to detachably couple the electronic device to a part of the body of the user, a contact exposed on one surface of the housing or the coupling member, which is in electrical connection with the battery, a temperature sensor electrically connected to the contact, and a circuit electrically connected to the battery, the contact, and the temperature sensor. The circuit may be configured to receive current generated by an external material through contact between the external material and the contact, charge the battery using the current based on a determination made based on the current that the voltage applied to at least part of the circuit is greater than or equal to a threshold, and sense temperature of the external material through the temperature sensor based on a determination that the voltage is less than the threshold.

According to an embodiment of the present disclosure, when the user wears the electronic device, one surface of the housing or the coupling member contacts the user.

According to an embodiment of the present disclosure, the electronic device may further include a conductive member electrically connected to the temperature sensor and the circuit.

According to an embodiment of the present disclosure, the circuit may be configured to correct the temperature of the external material based on the ambient temperature of the electronic device sensed through the conductive member.

According to an embodiment of the present disclosure, the conductive member may be an antenna radiator.

According to an embodiment of the present disclosure, the conductive member may be at least a part of the coupling member.

According to an embodiment of the present disclosure, an electronic device includes a housing, an external device connector including at least one contact exposed externally from the housing and electrically connected to an external electronic device, a conductive connection member connected to the at least one contact of the external device connector, and a first temperature sensor connected to the conductive connection member, for sensing temperature.

According to an embodiment of the present disclosure, the external device connector may include at least one port conforming to a USB communication protocol.

According to an embodiment of the present disclosure, the electronic device may further include a controller for receiving information related to the sensed temperature from the first temperature sensor and determining the received information to be a skin temperature.

According to an embodiment of the present disclosure, if the controller determines that the at least one contact contacts a part of the body of the user, the controller may determine information received from the first temperature sensor to be a skin temperature.

According to an embodiment of the present disclosure, if the controller determines that an external electronic device is connected to the at least one contact of the external device connector, the controller may disconnect the external device connector from the first temperature sensor.

According to an embodiment of the present disclosure, if the controller determines that an external electronic device is connected to the at least one contact of the external device connector, the controller may determine information received from the first temperature sensor to be a charging temperature.

According to an embodiment of the present disclosure, if charging is in progress through the external device connector, the controller may control the charging based on information received from the first temperature sensor.

According to an embodiment of the present disclosure, the electronic device may further include an antenna unit electrically connected to the controller and a second temperature sensor connected to the antenna unit, for sensing temperature.

According to an embodiment of the present disclosure, the controller may correct skin temperature determined by the first temperature sensor based on a temperature sensed by the second temperature sensor.

According to an embodiment of the present disclosure, if the controller determines that the antenna unit is in use, the controller may disconnect the antenna unit from the second temperature sensor.

Figure 4:
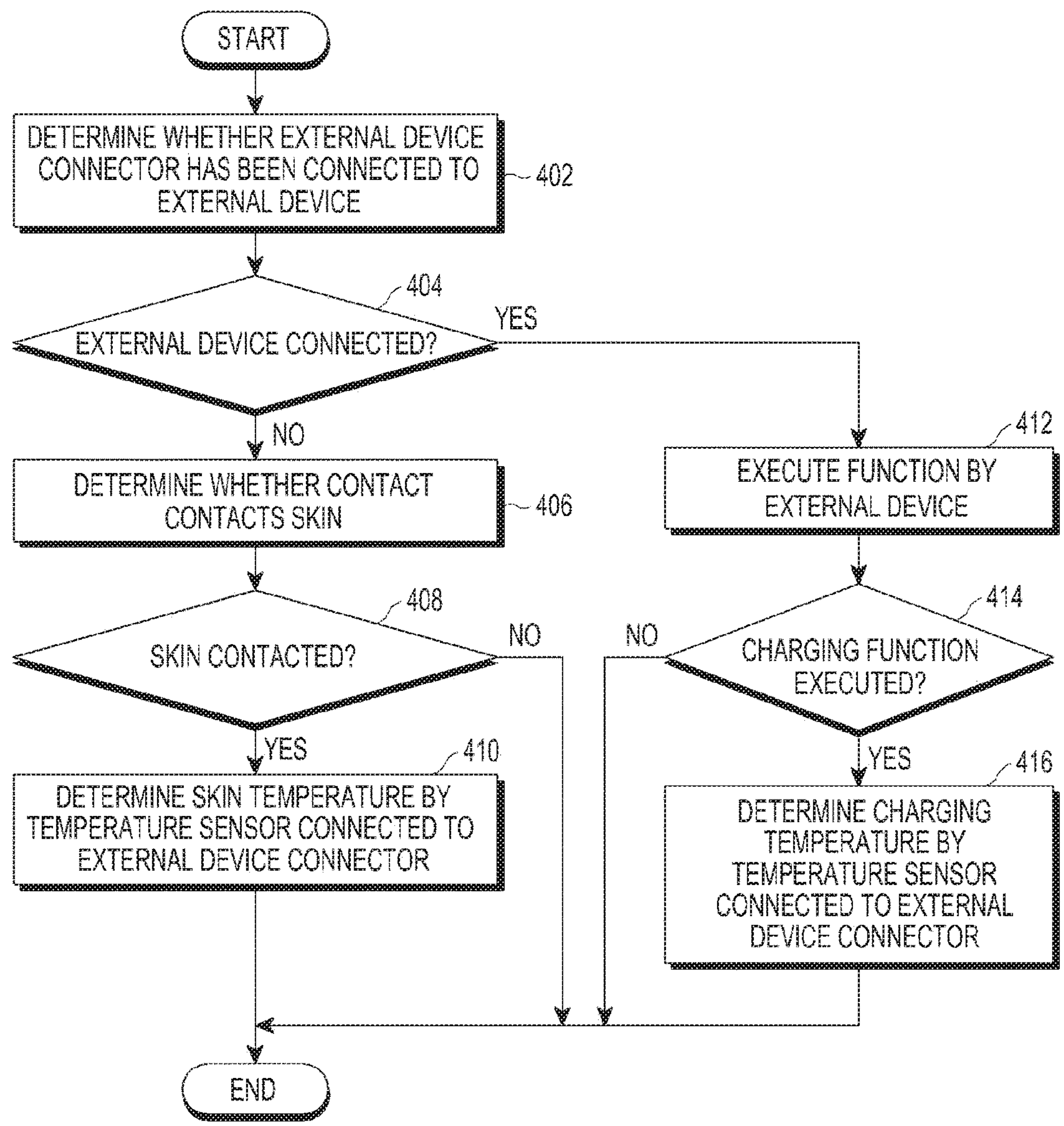
FIG. 4 is a flowchart of a method of determining temperature in an electronic device according to an embodiment of the present disclosure.

FIG. 4 is a flowchart of a method of determining temperature in an electronic device according to an embodiment of the present disclosure.

Referring to FIG. 4, the electronic device may determine whether the electronic device is connected to an external electronic device through an external device connector in step 402. If the electronic device determines that the electronic device is connected to an external electronic device in step 404, the electronic device may measure skin temperature through a temperature sensor connected to the external device connector according to an embodiment of the present disclosure.

For example, if the electronic device determines that the electronic device is not connected to an external electronic device in step 404, the electronic device may determine whether a contact of the external device connector contacts to the skin of a user in step 406. If the electronic device determines that the contact of the external device connector contacts the skin of the user in step 408, the electronic device may determine the skin temperature of the user by the temperature sensor connected to the external device connector in step 410.

In contrast, if the electronic device determines that the electronic device is connected to an external electronic device in step 404, the connected external electronic device may execute a function in step 412. If the electronic device determines that the connected external electronic device executes a charging function as a charger in step 414, the electronic device may determine a charging temperature by the temperature sensor connected to the external device connector in step 416.

According to various embodiments of the present disclosure, at least one of the steps listed in FIG. 4 may be omitted and at least one step may be added to the steps. Further, the steps of FIG. 4 may be performed in the depicted sequence or the sequence of at least one step and another step may be changed. The steps of FIG. 4 may be performed in the electronic device or in a server. In addition, at least one of the steps of FIG. 4 may be performed in the electronic device, while the remaining steps may be performed in the server.

According to an embodiment of the present disclosure, a method of an electronic device may include determining whether the electronic device is connected to an external electronic device by an external device connector having at least one contact exposed externally from a housing of the electronic device and electrically connected to the external electronic device, sensing temperature by a first temperature sensor connected to the at least one contact of the external device connector, and if it is determined that the external electronic device is not connected to the external device connector, determining the temperature sensed by the first temperature sensor to be the skin temperature of a user wearing the electronic device.

According to an embodiment of the present disclosure, the external device connector may include at least one port conforming to a USB communication protocol.

According to an embodiment of the present disclosure, if it is determined that the at least one contact contacts a part of the body of the user, information received from the first temperature sensor may be determined to be a skin temperature.

According to an embodiment of the present disclosure, if it is determined that an external electronic device is connected to the at least one contact of the external device connector, the external device connector may be disconnected from the first temperature sensor.

According to an embodiment of the present disclosure, if it is determined that an external electronic device is connected to the at least one contact of the external device connector, information received from the first temperature sensor may be determined to be a charging temperature.

According to an embodiment of the present disclosure, if charging is in progress through the external device connector, the charging may be controlled based on information received from the first temperature sensor.

According to an embodiment of the present disclosure, the method may further include sensing a temperature by a second temperature sensor connected to an antenna unit that is electrically connected to a controller.

According to an embodiment of the present disclosure, the method may further include correcting a skin temperature determined by the first temperature sensor based on a temperature sensed by the second temperature sensor.

According to an embodiment of the present disclosure, if it is determined that the antenna unit is in use, the antenna unit may be disconnected from the second temperature sensor.

Figure 5:
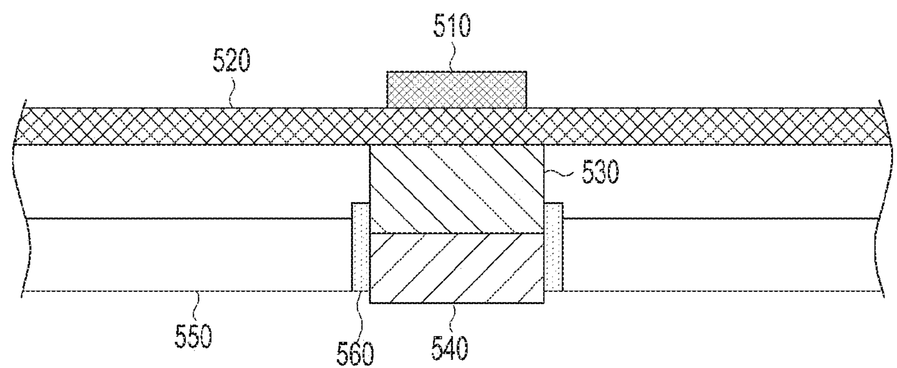
FIG. 5 is a cross-section of an electronic device for determining temperature according to an embodiment of the present disclosure.

FIG. 5 is a cross-section of an electronic device for determining temperature according to an embodiment of the present disclosure.

Referring to FIG. 5, the electronic device according to an embodiment of the present disclosure may include a housing 550 and a Printed Circuit Board (PCB) 520. The PCB 520 may be built into the housing 550 and at least one contact 540 may be exposed from at least a part of the housing 550. The at least one contact 540 may correspond to at least one port of the external device connector 320 illustrated in FIG. 3. The contact 540 may be exposed though an opening formed at a part of the housing 550 and fixed to the housing 550 by at least one fixing member 560.

The PCB 520 and the at least one contact 540 may be connected to each other by a conductive connection member 530. The conductive connection member 530 may include, or may be formed of, a material that can transfer electricity or heat. According to an embodiment of the present disclosure, the conductive connection member 530 may be shaped into an elastic form (for example, a C-clip or a Pogo pin) or may include or be formed of an elastic material. For example, the contact 540 fixed to the housing 550 may be electrically connected to the PCB 520 without being apart from the PCB 520 by the elasticity of the conductive connection member 530. The conductive connection member 530 may be fixed or attached to the PCB 520.

According to an embodiment of the present disclosure, a temperature sensor 510 may be disposed opposite to the contact 540 with respect to the PCB 520. The temperature sensor 510 may be connected to the PCB 520 directly or indirectly. For example, the temperature sensor 510 may be attached or fixed to the PCB 520. According to an embodiment of the present disclosure, the temperature sensor 510 may be fixed in the form of a semiconductor Integrated Circuit (IC) or chip to the PCB 52. Also, if at least one pin or temperature pad of the temperature sensor 510 contacts the conductive connection member 530, the temperature sensor 510 may sense heat transferred from the contact 540.

According to an embodiment of the present disclosure, if the user wears the electronic device and thus the contact 540 contacts the skin of the user, heat of the skin of the user may be transferred to the temperature sensor 510 through the conductive connection member 530 and the PCB 520. According to an embodiment of the present disclosure, since the temperature sensor 510 is disposed nearest to the contact 40 that is configured to contact the skin of the user as illustrated in FIG. 5, a skin temperature can be measured with high reliability. According to an embodiment of the present disclosure, the temperature sensor 510 may be disposed between the PCB 520 and the housing 550.

According to an embodiment of the present disclosure, if an external electronic device such as a charger contacts the contact 540, charging power supplied through the charger may be supplied to the PCB 520 through the conductive connection member 530. For example, charging power supplied through a circuit formed on the PCB 520 may be transferred to a battery or a rechargeable battery.

Figure 6:
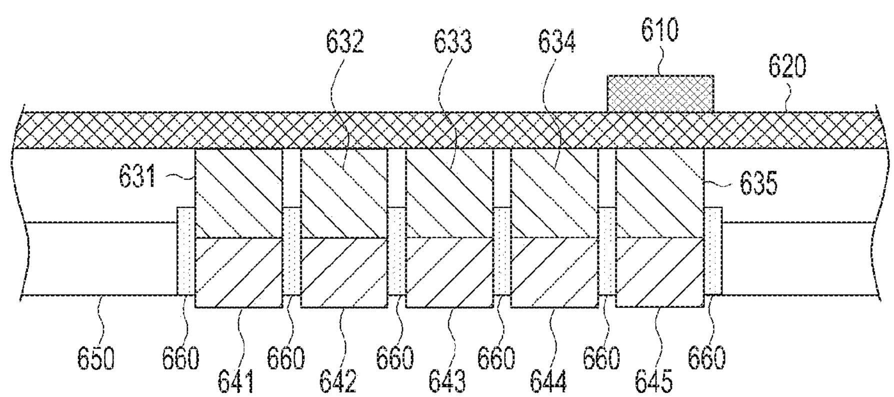
FIG. 6 is a cross-section of an electronic device for determining temperature according to an embodiment of the present disclosure.

FIG. 6 is a cross-section of an electronic device for determining temperature according to an embodiment of the present disclosure.

Referring to FIG. 6, the electronic device according to an embodiment of the present disclosure may include a housing 650 and a PCB 620. The PCB 620 may be built into the housing 650 and at least one contact (for example, a first to fifth contacts 641, 642, 643, 644, and 645 in FIG. 6) may be exposed from at least a part of the housing 650. The first to fifth contacts 641, 642, 643, 644, and 645 may correspond to at least one port of the afore-described external device connector.

For example, the first to fifth contacts 641, 642, 643, 644, and 645 may correspond to a Voltage Bus (VBUS) port, a negative differential data (D−) port, a positive differential data (D+) port, an ID port, and a ground (GND) port, respectively. According to an embodiment of the present disclosure, at least one of the plurality of contacts may be omitted or at least one other port may be added to the plurality of contacts.

For example, the plurality of ports may be pins supporting communication conforming to at least one communication protocol. The communication protocol may be a USB communication protocol or a micro USB communication protocol, which should not be construed as limiting the present disclosure.

For example, the electronic device may supply or receive power to or from a contacted external electronic device through the VBUS port. The electronic device may transmit and/or receive data to or from the external electronic device through the D− port or the D+ port.

The electronic device may determine whether it is connected to an external electronic device or the type of a connected external electronic device, through the ID port.

According to an embodiment of the present disclosure, the function of each port may be set as listed in Table 1 below. However, the present disclosure is not limited to the wiring assignment listed in Table 1 below.

TABLE 1

| Contact Number | Signal Name | Typical Wiring Assignment |
|---|---|---|
| 1 | VBUS | Red |
| 2 | D- | White |
| 3 | D- | Green |
| 4 | ID | <Ra_PLUG_ID |
| 5 | GND | Black |
| Shell | Shield | Drain Wire |

Each of the first to fifth contacts 641, 642, 643 644, and 645 may be exposed though an opening formed at a part of the housing 650 and fixed to the housing 650 by at least one fixing member 660.

One or more of the first to fifth contacts 641, 642, 643 644, and 645 may be connected to the PCB 620 respectively by first to fifth conductive connection members 631, 632, 633, 634, and 635. The first to fifth conductive connection members 631, 632, 633, 634, and 635 may include or be formed of a material that can transfer electricity or heat. According to an embodiment of the present disclosure, each of the first to fifth conductive connection members 631, 632, 633, 634, and 635 may be shaped into an elastic form (for example, a C-clip or a Pogo pin) or may include or be formed of an elastic material. For example, the first to fifth contacts 641, 642, 643, 644, and 645 fixed to the housing 650 may be electrically connected to the PCB 620 without being apart from the PCB 620 by the elasticity of the first to fifth conductive connection members 631, 632, 633, 634, and 635.

Each of the first to fifth conductive connection members 631, 632, 633, 634, and 635 may be fixed or attached to the PCB 620.

According to an embodiment of the present disclosure, a temperature sensor 610 may be disposed opposite to the first to fifth contacts 641, 642, 643, 644, and 645 with respect to the PCB 620. The temperature sensor 610 may be connected to the PCB 620 directly or indirectly. For example, the temperature sensor 610 may be attached or fixed to the PCB 620. According to an embodiment of the present disclosure, the temperature sensor 610 may be fixed in the form of a semiconductor chip to the PCB 620. In addition, as at least one pin or temperature pad of the temperature sensor 610 contacts the first to fifth conductive connection members 631, 632, 633, 634, and 635, the temperature sensor 610 may sense heat transferred from at least one of the first to fifth contacts 641, 642, 643, 644, and 645.

According to an embodiment of the present disclosure, if the user wears the electronic device and thus at least one of the first to fifth contacts 641, 642, 643, 644, and 645 contacts the skin of the user, heat from the skin of the user may be transferred to the temperature sensor 610 through at least one of the first to fifth conductive connection members 631, 632, 633, 634, and 635 and the PCB 620. According to an embodiment of the present disclosure, since the temperature sensor 610 is disposed nearest to at least one of the first to fifth contacts 641, 642, 643, 644, and 645 that are configured to contact the skin of the user as illustrated in FIG. 6, a skin temperature can be measured with high reliability. According to an embodiment of the present disclosure, the temperature sensor 610 may be disposed between the PCB 620 and the housing 650.

According to an embodiment of the present disclosure, if an external electronic device such as a charger contacts at least one of the first to fifth contacts 641, 642, 643, 644, and 645, charging power supplied through the charger may be supplied to the PCB 620 through the at least one of the first to fifth conductive connection members 631, 632, 633, 634, and 635. For example, charging power supplied through a circuit formed on the PCB 620 may be transferred to a battery or a rechargeable battery.

Figure 7:
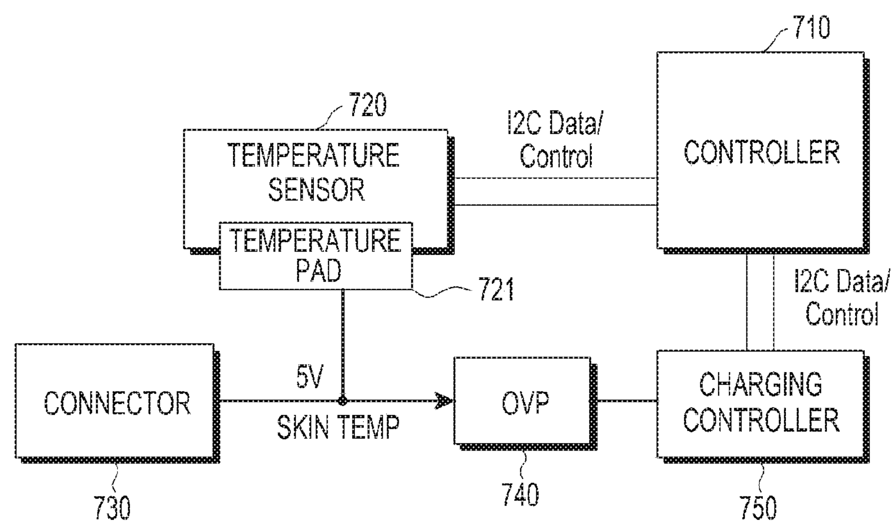
FIG. 7 is a block diagram of an electronic device according to an embodiment of the present disclosure.

FIG. 7 is a block diagram of an electronic device according to an embodiment of the present disclosure.

Referring to FIG. 7, the electronic device according to an embodiment of the present disclosure may include at least one of a controller 710, a temperature sensor 720, a connector 730, an Over Voltage Protector (OVP) 740, and a charging controller 750.

The controller 710 illustrated in FIG. 7 may correspond to the controller 210 or 310 illustrated in FIG. 2 and FIG. 3, respectively, and the connector 730 may correspond to the external device connector 220 or 320 illustrated in FIG. 2 and FIG. 3 respectively. The temperature sensor 720 may correspond to the temperature sensor 230 or 330 illustrated in FIG. 2 and FIG. 3, respectively.

According to an embodiment of the present disclosure, if the skin of a user contacts at least one contact of the connector 730 (for example, if the user wears the electronic device), heat from the skin of the user may be transferred to a temperature pad 721 of the temperature sensor 720 through a USB 5V line of a Pogo connector structure. The temperature sensor 720 may sense a temperature from the heat received through the temperature pad 721 and transmit information about the sensed temperature (for example, a digitized temperature value) to the controller 710. The controller 710 may receive the temperature information from the temperature sensor 720 and determine the skin temperature of the user based on the received temperature information.

According to an embodiment of the present disclosure, if an external electronic device (for example, a charger) is connected to or contacts the connector 730 and thus the controller 710 determines a charging state, the controller 710 may determine a temperature sensed through the temperature sensor 720 to not be a skin temperature but a charging temperature. According to an embodiment of the present disclosure, since charging is not performed during measurement of skin temperature as described above, a heat transfer path from the connector 730 to the charging controller 750 may be blocked by switching using an Over Voltage Lock Out (OVLO) function of the OVP 740, thereby minimizing the effect of heat-emitting parts inside a PCB.

According to an embodiment of the present disclosure, if charging is performed without measuring a skin temperature, the controller 710 may determine a temperature sensed by the temperature sensor 720 to not be a skin temperature but a charging temperature. For example, if the electronic device is being charged, the temperature sensor 720 may act as a thermistor.

Figure 8:
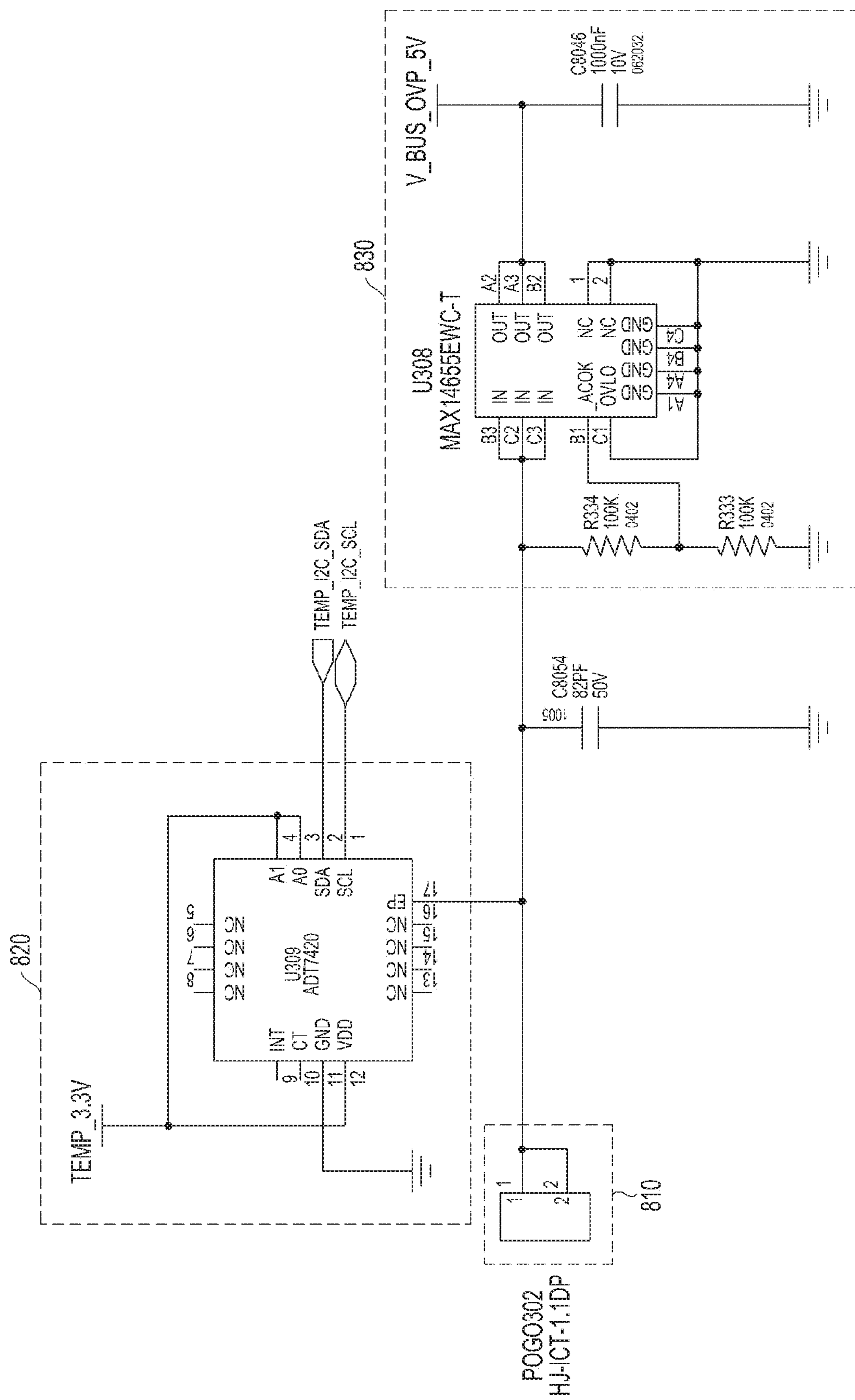
FIG. 8 is a circuit diagram of an electronic device according to an embodiment of the present disclosure.

FIG. 8 is a circuit diagram of an electronic device according to an embodiment of the present disclosure.

Referring to FIG. 8, the electronic device according to an embodiment of the present disclosure may include an external device connector 810 having at least one contact, a temperature sensor 820, and an OVP 830. Each of the temperature sensor 820 and the OVP 830 may include at least one IC as illustrated in FIG. 8. The temperature sensor 820 or the OVP 830 may use at least one known IC or may be configured as a new semiconductor chip (for example, an IC), a device, or a circuit including at least one device. A detailed description of each IC for the temperature sensor 820 or the OVP 830 illustrated in FIG. 8 is not provided herein.

A charging terminal of the external device connector 810 may be connected to a charging controller through the OVP 830. According to an embodiment of the present disclosure, the charging terminal of the external device connector 810 may be connected to the temperature sensor 820. According to an embodiment of the present disclosure, when a charger is connected to or contacts the charging terminal of the external device connector 810, a charging operation may be performed on a rechargeable battery through the OVP 830. If charging is in progress, a temperature sensed by the temperature sensor 820 may be determined to be a charging temperature according to an embodiment of the present disclosure. According to an embodiment of the present disclosure, a path from the external device connector 810 to the temperature sensor 820 may be blocked.

According to an embodiment of the present disclosure, if the charging terminal of the external device connector 810 contacts the skin of a user, a temperature sensed by the temperature sensor 820 may be determined to be the skin temperature of the user. According to an embodiment of the present disclosure, if the temperature sensor 820 senses a skin temperature, the OVP 820 may block a heat transfer path to the charging controller (for example, a path through one of pins A2, A3, and B2), thereby minimizing the effect of heat-emitting parts inside a PCB and enabling the temperature sensor 820 to sense skin temperature reliably.

Figure 9:
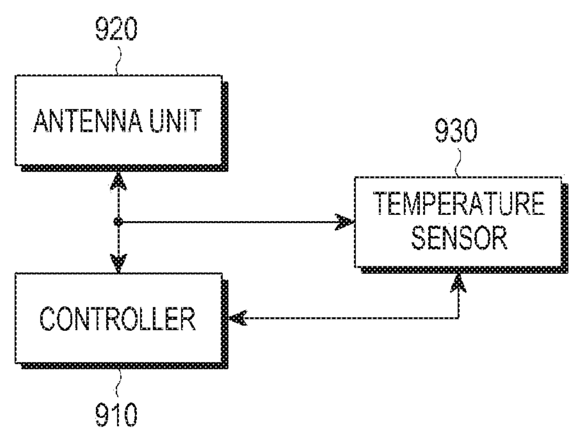
FIG. 9 is a block diagram of an electronic device according to an embodiment of the present disclosure.

FIG. 9 is a block diagram of an electronic device according to an embodiment of the present disclosure.

Referring to FIG. 9, the electronic device according to an embodiment of the present disclosure may include at least one of a controller 910, an antenna unit 920, or a temperature sensor 930.

All or part of a function of each component in the electronic device illustrated in FIG. 9 may be included in at least one component illustrated in FIG. 1. For example, at least a part of the controller 910 may be included in the processor 120 of FIG. 1. Also, at least a part of the antenna unit 920 may be included in the communication interface 170 illustrated in FIG. 1. The temperature sensor 930 may correspond to the temperature sensor 180 illustrated in FIG. 1. The antenna unit 920 may be connected electrically to the controller 910 or the temperature sensor 930.

According to an embodiment of the present disclosure, the electronic device may transmit and receive data wirelessly to and from an external electronic device through the antenna unit 920.

The controller 910 may control the electronic device to communicate with the external electronic device through the antenna unit 920 and may process data received from the external electronic device. At least a part of the functions of the controller 910 may be included in the processor 120 illustrated in FIG. 1.

According to an embodiment of the present disclosure, the temperature sensor 930 may be connected to the antenna unit 920 directly or indirectly. For example, the antenna unit 920 and the temperature sensor 930 may be connected to each other by direct contact or by means of a conductive material. For example, the temperature sensor 930 may be connected to at least a part of an antenna pad provided in the antenna unit 920 directly or indirectly.

The temperature sensor 930 may sense a temperature of the antenna unit 920 through a connection to the antenna unit 920. For example, the ambient temperature of the electronic device may be sensed by sensing temperature of the antenna unit 920. Information related to the temperature sensed by the temperature sensor 930 may be transmitted to the controller 910.

The controller 910 may receive the information related to the measured temperature from the temperature sensor 930 and may subject the received information to various processes. The controller 910 may control an operation of the temperature sensor 930. The controller 910 may control an operation of the temperature sensor 930 or use the information related to the temperature received from the temperature sensor 930 according to an operation state or control state of the antenna unit 920.

According to an embodiment of the present disclosure, if the controller 910 determines that no communication function is performed with any external device through the antenna unit 920, the controller 910 may determine a temperature measured by the temperature sensor 930 to be the ambient temperature of the electronic device. According to an embodiment of the present disclosure, when the controller 910 is to measure the ambient temperature of the electronic device through the temperature sensor 930, the controller 910 may shut-off a circuit, connected to the antenna unit 920, to other structures of the electronic device in order to determine an accurate ambient temperature.

Figure 10:
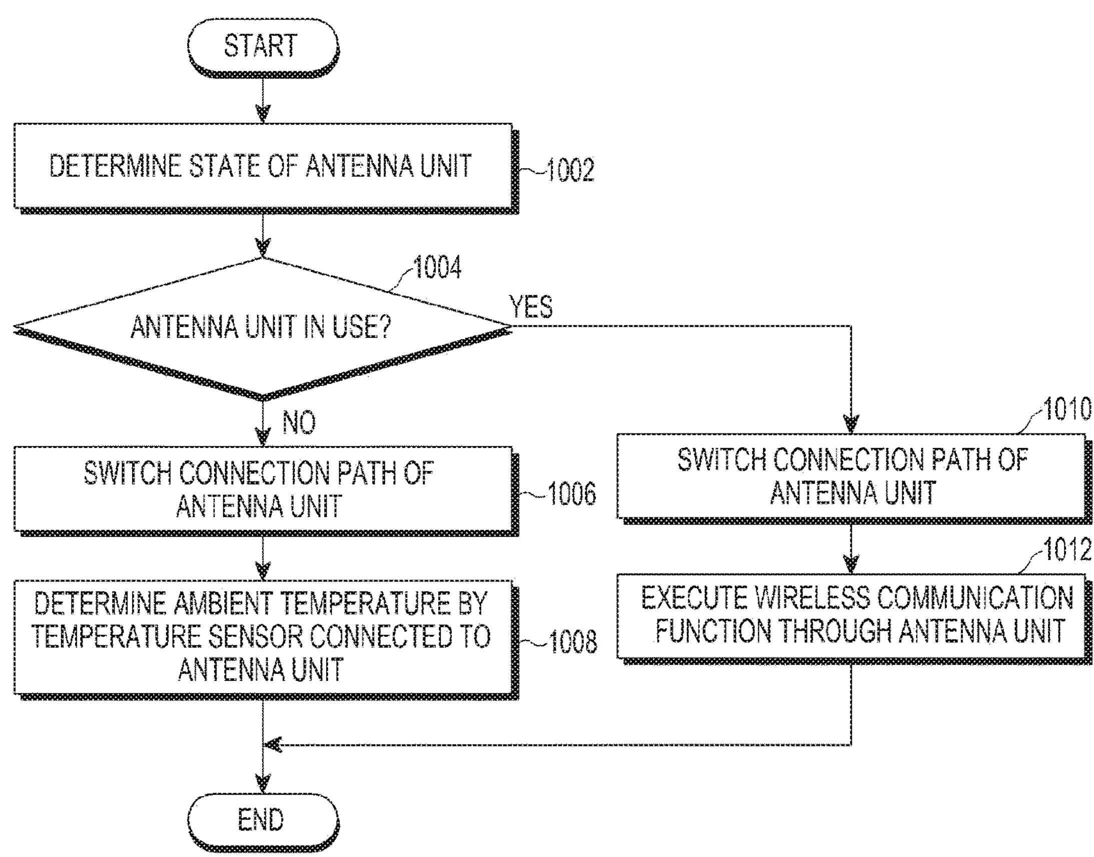
FIG. 10 is a flowchart of a method of determining a temperature in an electronic device according to an embodiment of the present disclosure.

FIG. 10 is a flowchart of a method of determining temperature in an electronic device according to an embodiment of the present disclosure.

Referring to FIG. 10, a state of an antenna unit may be determined in step 1002. If it is determined that the antenna unit is being used in step 1004, a connection path of the antenna unit may be switched in step 1010 and a wireless communication function may be performed through the antenna unit in step 1012. For example, if it is determined that the antenna unit is being used in step 1004, a connection of the antenna unit to a PCB or a controller of the electronic device may be controlled. According to an embodiment of the present disclosure, a connection path between the antenna unit and a temperature sensor may be blocked.

In contrast, if it is determined that the antenna unit is not being used in step 1004, the connection path of the antenna unit may be switched in step 1006 and the ambient temperature may be sensed by the temperature connected to the antenna unit in step 1008. For example, if it is determined that the antenna unit is not being used in step 1004, the antenna unit may be disconnected from the PCB or the controller of the electronic device.

Figure 11:
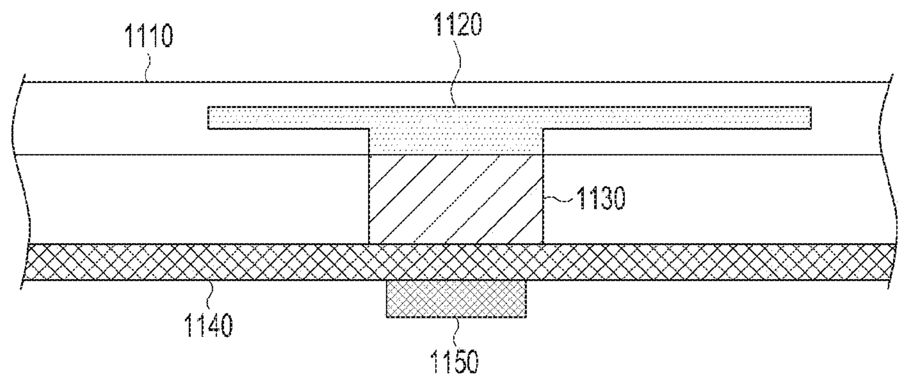
FIG. 11 is a cross-section of an electronic device for determining a temperature according to an embodiment of the present disclosure.

FIG. 11 is a cross-section of an electronic device for determining temperature according to an embodiment of the present disclosure.

Referring to FIG. 11, the electronic device according to an embodiment of the present disclosure may include a housing 1110 and a PCB 1140. The PCB 1140 may be built into the housing 1110 and an antenna 1120 may be included inside the housing 1110. For example, the antenna 1120 may be fabricated in such a manner that the antenna 1120 may be integrated with the housing 1110 by a process such as double molding, In Mold Antenna (IMA), Laser Direct Structuring (LDS), or the like during fabrication, which should not be construed as limiting an embodiment of the present disclosure.

At least a part of the antenna unit 110 may be connected to the PCB 1140 by a conductive connection member 1130. The conductive connection member 1130 may include or be formed of a material that can transfer electricity or heat. According to an embodiment of the present disclosure, the conductive connection member 1130 may be shaped into an elastic form (for example, a C-clip or a Pogo pin) or may include or be formed of an elastic material. For example, the antenna unit 1120 fixed to the housing 1110 may be electrically connected to the PCB 1140 without being apart from the PCB 1140 by the elasticity of the conductive connection member 1130. The conductive connection member 1130 may be fixed or attached to the PCB 1140.

According to an embodiment of the present disclosure, a temperature sensor 1150 may be disposed opposite to the antenna unit 1120 with respect to the PCB 1140. The temperature sensor 1150 may be connected to the PCB 1140 directly or indirectly. For example, the temperature sensor 1150 may be attached or fixed to the PCB 1140.

According to an embodiment of the present disclosure, if a communication function is not executed through the antenna unit 1120 or the ambient temperature of the electronic device is to be measured, heat from the antenna unit 1120 may be transferred to the temperature sensor 1150 through the conductive connection member 1130 and the PCB 1140. According to an embodiment of the present disclosure, since the temperature sensor 1150 is disposed near to the antenna unit 1120 which is structurally nearest to the outside of the electronic device as illustrated in FIG. 11, the ambient temperature can be measured with high reliability. According to an embodiment of the present disclosure, the temperature sensor 1150 may be disposed between the PCB 1140 and the housing 1110.

Figure 12:
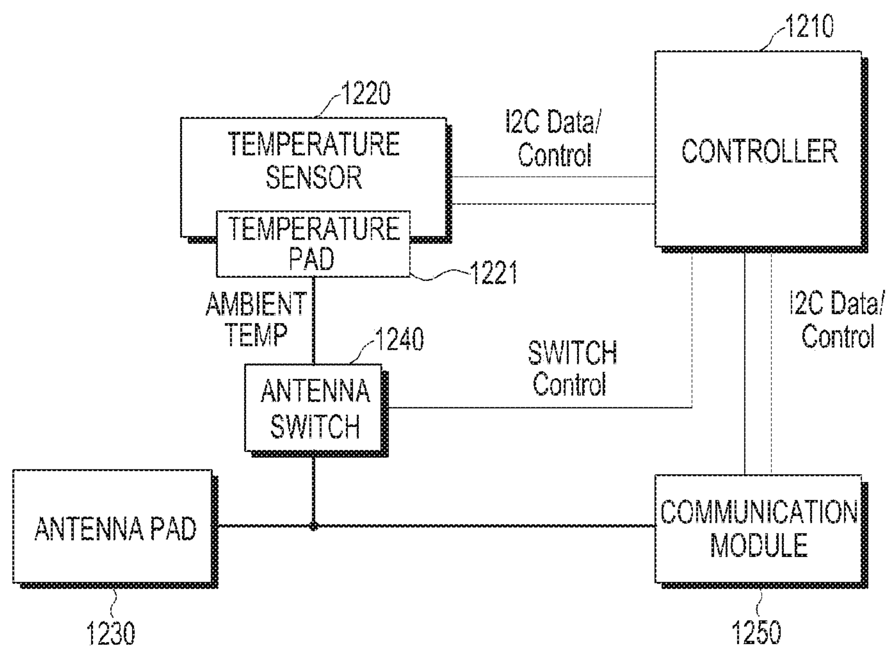
FIG. 12 is a block diagram of an electronic device according to an embodiment of the present disclosure.

FIG. 12 is a block diagram of an electronic device according to an embodiment of the present disclosure.

Referring to FIG. 12, the electronic device according to an embodiment of the present disclosure may include at least one of a controller 1210, a temperature sensor 1220, a temperature pad 1221, an antenna pad, an antenna switch 1240, and a communication module 1250.

According to an embodiment of the present disclosure, if the controller 1210 determines that data transmission and reception is in progress through the antenna pad 1230, the controller 1210 may block a path between the antenna pad 1230 and the temperature sensor 1220 by controlling the antenna switch 1240.

According to an embodiment of the present disclosure, if the ambient temperature is to be measured without using a data transmission and function through the antenna pad 1230, a path may be connected between the antenna pad 1230 and the temperature sensor 1220 by controlling the antenna switch 1240. According to an embodiment of the present disclosure, if the ambient temperature is to be measured, the controller 1210 may block a path between the antenna pad 1230 and the communication module 1250, thereby enabling the temperature sensor 1220 to sense the ambient temperature reliably.

According to an embodiment of the present disclosure, the temperature sensor 1220 may sense the ambient temperature using an antenna nearest the air around the electronic device. For example, the ambient temperature measured in a structure such as a Multipoint Distribution System (MDS) of an antenna may be transmitted to the temperature sensor 1220 that contacts or is close to the PCB through an antenna contact (pad) and the ambient temperature measured by the temperature sensor 1220 may be transmitted to the controller 1210 through a communication interface such as an Inter-Integrated Circuit (I2C). Thus, the sensed ambient temperature information may be used in the controller 1210.

According to an embodiment of the present disclosure, if an antenna is used to measure the ambient temperature, a signal transmission and reception path may be controlled using the antenna switch 1240, in consideration of a change in a Reception/Transmission (Rx/Tx) situation and an antenna matching change.

Figure 13:
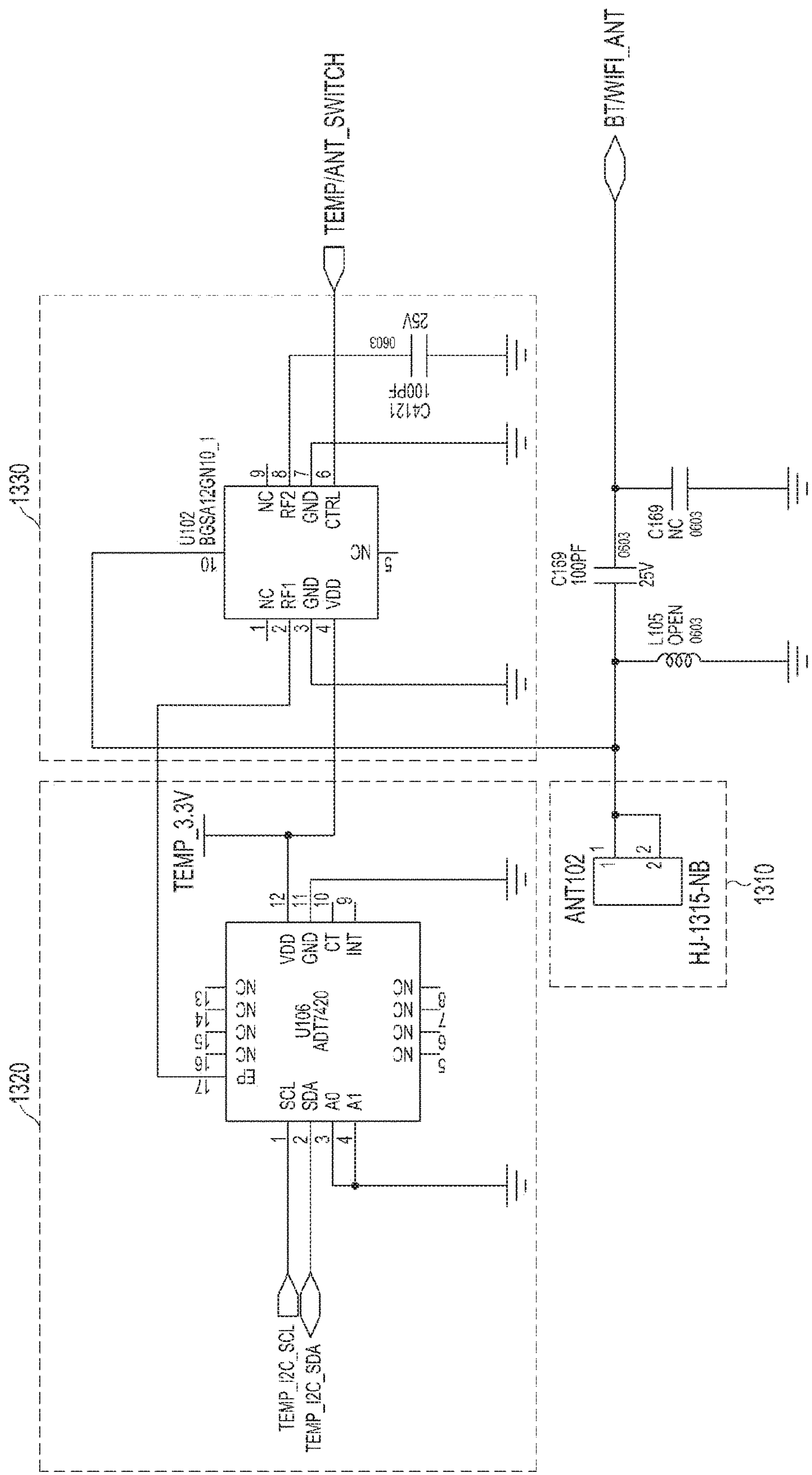
FIG. 13 is a circuit diagram of an electronic device according to an embodiment of the present disclosure.

FIG. 13 is a circuit diagram of an electronic device according to an embodiment of the present disclosure.

Referring to FIG. 13, the electronic device according to an embodiment of the present disclosure may include a connection terminal 1310, a temperature sensor 1320, and an antenna switching unit 1330. The temperature sensor 1320 or the antenna switching unit 1330 may include at least one IC as illustrated in FIG. 13.

The temperature sensor 1320 or the antenna switching unit 1330 may use at least one known IC or may be configured as a new semiconductor chip (for example, an IC), a device, or a circuit including at least one device. A detailed description of a detailed structure and operation of each IC for the temperature sensor 1320 or the antenna switching unit 1330 illustrated in FIG. 13 is not provided herein.

The connection terminal 1310 of the antenna unit may be connected to a controller or a communication module that may process a transmission signal or a received signal through the antenna switching unit 1330. According to an embodiment of the present disclosure, the connection terminal 1310 of the antenna unit may be connected to the temperature sensor 1320 through the antenna switching unit 1330. According to an embodiment of the present disclosure, if the antenna unit is in use, the antenna switching unit 1330 may connect the connection terminal 1310 of the antenna unit to the controller or the communication module. According to an embodiment of the present disclosure, the antenna switching unit 1330 may block a path from the connection terminal 1310 of the antenna unit to the temperature sensor 1320.

According to an embodiment of the present disclosure, if the antenna unit is not in use or the ambient temperature is to be measured, the antenna switching unit 1330 may connect the connection terminal 1310 of the antenna unit to the temperature sensor 1320, as described above. If the ambient temperature is to be measured, the antenna switching unit 1330 may block a path from the connection unit 1310 of the antenna unit to the controller or the communication module, thereby enabling the temperature sensor 1320 to sense ambient temperature reliably.

Figure 14:
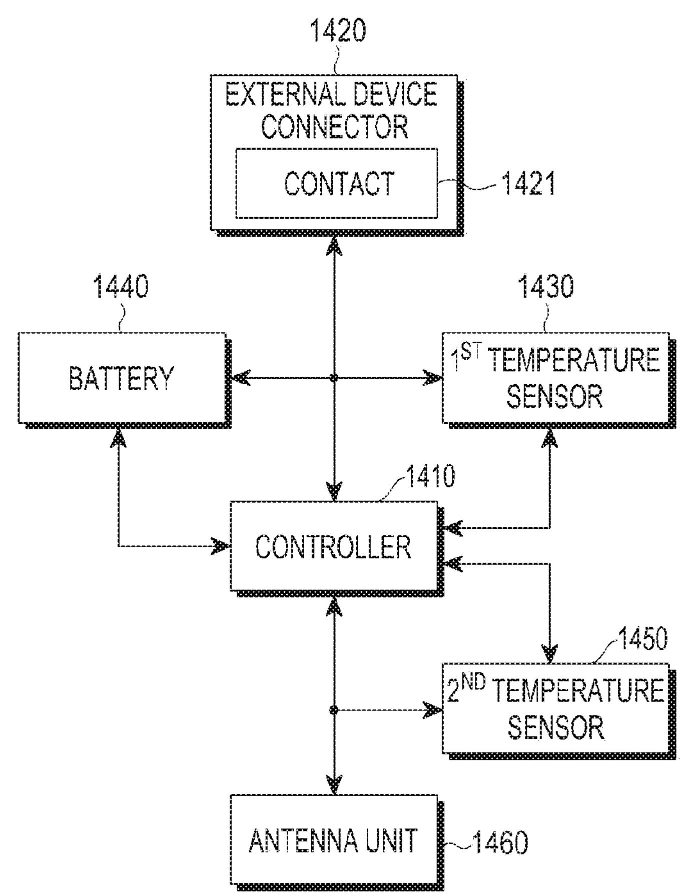
FIG. 14 is a block diagram of an electronic device according to an embodiment of the present disclosure.

FIG. 14 is a block diagram of an electronic device according to an embodiment of the present disclosure.

Referring to FIG. 14, the electronic device according to an embodiment of the present disclosure may include at least one of a controller 1410, an external device connector 1420, a first temperature sensor 1430, a battery 1440, a second temperature sensor 1450, and an antenna unit 1460.

All or part of a function of each component in the electronic device illustrated in FIG. 14 may be included in at least one component illustrated in FIG. 1. For example, at least a part of the controller 1410 may be included in the processor 120 of FIG. 1. In addition, at least part of the external device connector 1420 may be included in the I/O interface 150 or the communication interface 170 illustrated in FIG. 1. The external device connector 1420 may be connected electrically to the controller 1410 or the first temperature sensor 1430. At least a part of the antenna unit 1460 may correspond to the communication interface 170 illustrated in FIG. 1. The antenna unit 1460 may be connected electrically to the controller 1410 or the second temperature sensor 1450.

According to an embodiment of the present disclosure, the electronic device may be electrically connected to an external electronic device through the external device connector 1420. At least a part of the controller 1410, the external device connector 1420, or the first temperature sensor 1430 illustrated in FIG. 14 may execute the same function as the controller 210, the external device connector 220, or the temperature sensor 230 illustrated in FIG. 2. In addition, at least a part of the controller 1410, the antenna unit 1460, or the second temperature sensor 1450 illustrated in FIG. 14 may execute the same function as the controller 910, the antenna unit 920, or the temperature sensor 930 illustrated in FIG. 9. The following description is given of FIG. 14, with a description of the same functions described in FIG. 2 or FIG. 9 omitted.

According to an embodiment of the present disclosure, at least one of a plurality of contacts 1421 included in the external device connector 1420 may be connected to the battery 1440. For example, if a charger is connected to the external device connector 1420, for charging the electronic device, power supplied from the charger is transferred to the battery 1440, thus charging the battery 1440.

According to an embodiment of the present disclosure, if the controller 1410 determines that the charger has been connected to the external device connector 1420 or a voltage greater than or equal to a predetermined voltage is applied through the external device connector 1420, the controller 1410 may determine that the charger has been connected. According to an embodiment of the present disclosure, if the battery 1440 is being charged through the external device connector 1420, a temperature measured through the first temperature sensor 1430 may be determined to not be a skin temperature but a charging temperature. For example, if a charging temperature is determined through the first temperature sensor 1430 during charging, information related to the temperature measured through the first temperature sensor 1430 may be used as information for preventing over-temperature of the battery 1440.

According to an embodiment of the present disclosure, if the battery 1440 is being charged through the external device connector 1420, the first temperature sensor 1430 may be disconnected from the external device connector 1420. The antenna unit 1460 may be connected electrically to the controller 1410 or the second temperature sensor 1450.

According to an embodiment of the present disclosure, the electronic device may transmit and receive data wirelessly to and from an external electronic device through the antenna unit 1460.

The controller 1410 may control the electronic device to communicate with the external electronic device through the antenna unit 1460 and may process data received from the external electronic device. At least a part of functions of the controller 1410 may be included in the processor 120 illustrated in FIG. 1.

According to an embodiment of the present disclosure, the second temperature sensor 1450 may be connected to the antenna unit 1460 directly or indirectly. For example, the antenna unit 1460 and the second temperature sensor 1450 may be connected to each other by direct contact or by means of a conductive material. For example, the second temperature sensor 1450 may be connected to at least a part of an antenna pad provided in the antenna unit 1460 directly or indirectly.

The second temperature sensor 1450 may sense the temperature of the antenna unit 1460 through a connection to the antenna unit 1460. For example, the ambient temperature of the electronic device may be sensed by sensing the temperature of the antenna unit 1460. Information related to the temperature sensed by the second temperature sensor 1450 may be transmitted to the controller 1410.

The controller 1410 may receive the information related to the measured temperature from the second temperature sensor 1450 and may subject the received information to various processes. For example, a skin temperature sensed by the first temperature sensor 1430 may be corrected to a more accurate value by reflecting ambient temperature sensed by the second temperature sensor 1450 in the skin temperature sensed by the first temperature sensor 1430.

The controller 1410 may control an operation of the second temperature sensor 1450, and may control an operation of the second temperature sensor 1450 according to an operation state or control state of the antenna unit 1460 or use information related to the temperature received from the second temperature sensor 1450.

According to an embodiment of the present disclosure, if the controller 1410 determines that no communication function is performed with any external device through the antenna unit 1460, the controller 1410 may determine a temperature sensed by the second temperature sensor 1450 to be the ambient temperature of the electronic device. According to an embodiment of the present disclosure, when the controller 1410 is to measure the ambient temperature of the electronic device through the second temperature sensor 1450, the controller 1410 may shut-off a circuit connected from the antenna unit 1460 to other structures of the electronic device in order to determine an accurate ambient temperature.

According to an embodiment of the present disclosure, the first temperature sensor 1430 and the second temperature sensor 1450 may be configured separately as illustrated in FIG. 14 or into one sensor. If the first temperature sensor 1430 and the second temperature sensor 1450 are configured into one sensor, the controller 1410 may determine temperature sensed by a single temperature sensor to be a skin temperature, the ambient temperature, or a charging temperature according to a current operation state of the electronic device (for example, a connection state of the external device connector 1420, changing or non-charging, and use or non-use of the antenna unit 1460).

Figure 15:
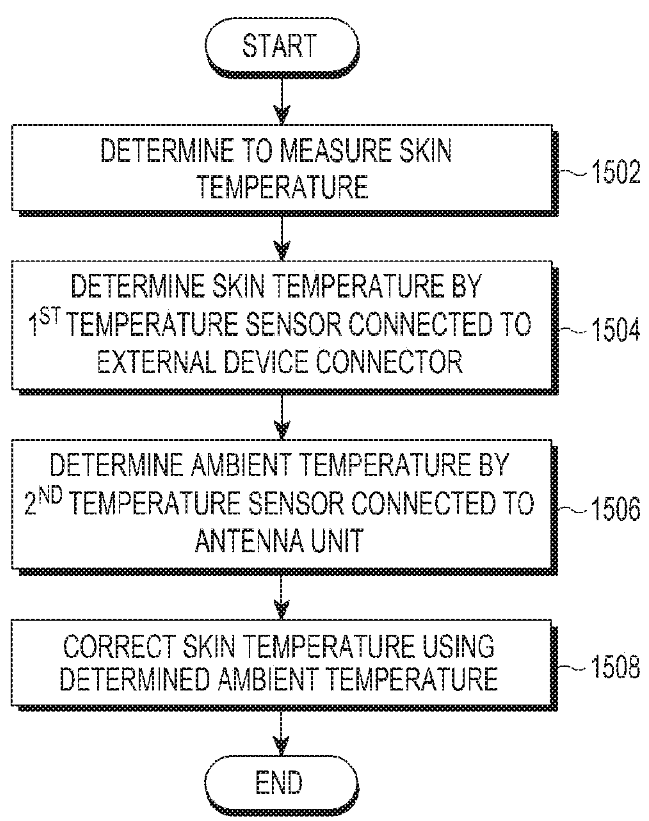
FIG. 15 is a flowchart of a method of determining a temperature in an electronic device according to an embodiment of the present disclosure.

FIG. 15 is a flowchart of a method of determining a temperature in an electronic device according to an embodiment of the present disclosure.

Referring to FIG. 15, it may be determined whether to measure skin temperature in step 1502. The determination to measure skin temperature may be made by a user selecting an option to measure skin temperature. Skin temperature may be measured in a predetermined state (for example, when the contact of the external device connector contacts the skin of the user). Alternatively, skin temperature may be measured at predetermined intervals.

In step 1504, if it is determined to measure skin temperature, a skin temperature may be determined by a first temperature sensor connected to an external device connector. The ambient temperature may be determined by a second temperature sensor connected to an antenna unit in step 1506. The skin temperature may be corrected by the determined ambient temperature in step 1508.

Figure 16:
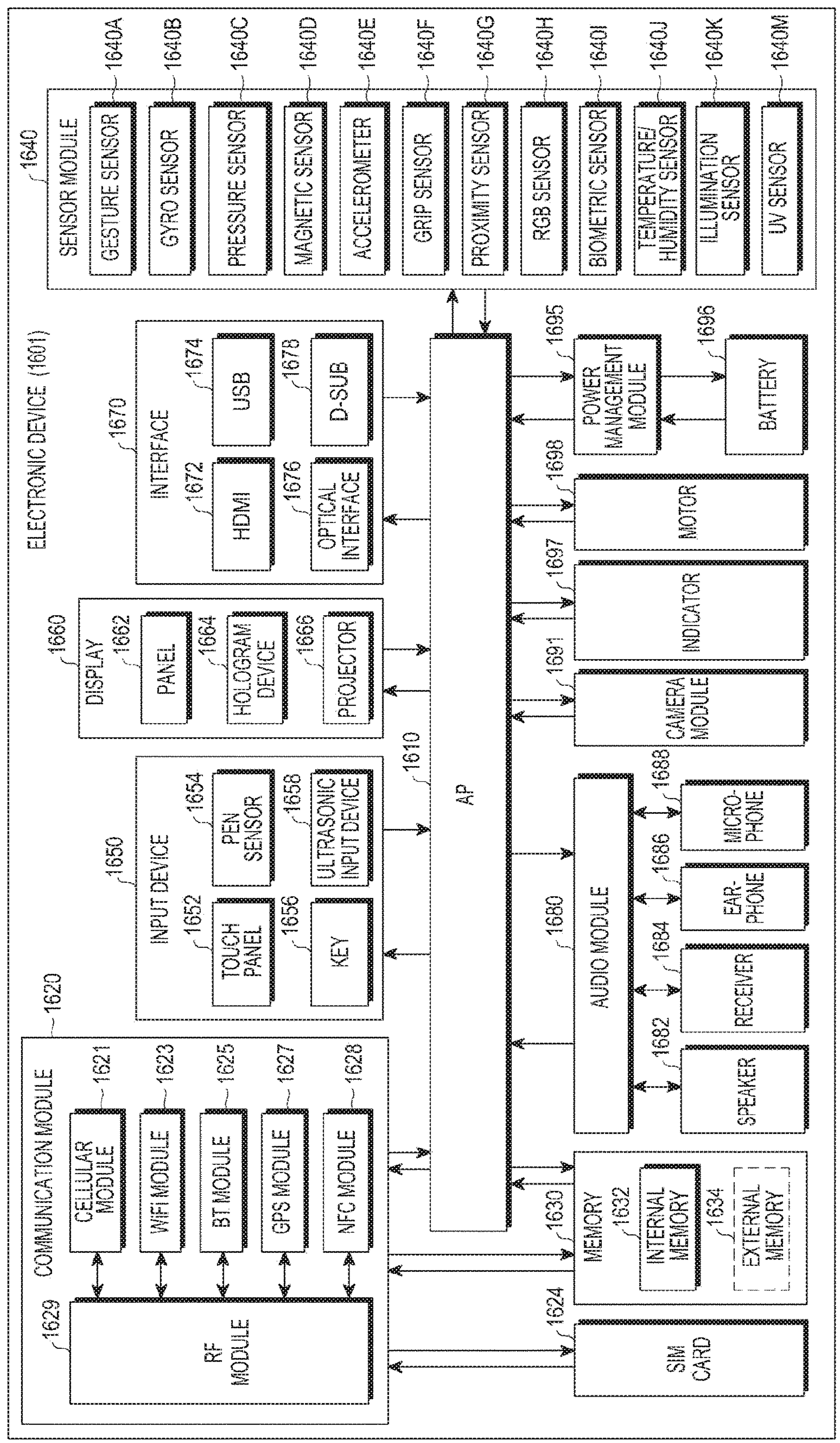
FIG. 16 is a block diagram of an electronic device according to an embodiment of the present disclosure.

FIG. 16 is a block diagram of an electronic device 1601 according to an embodiment of the present disclosure. The electronic device 1601 may include, for example, all or part of the electronic devices illustrated in FIG. 1, 2, 3, 7, 9, 12 or 14.

Referring to FIG. 16, the electronic device 1601 may include at least one Application Processor (AP) 1610, a communication module 1620, a Subscriber Identification Module (SIM) card 1624, a memory 1630, a sensor module 1640, an input device 1650, a display 1660, an interface 1670, an audio module 1680, a camera module 1691, a power management module 1695, a battery 1696, an indicator 1697, and a motor 1698.

The AP 1610 may, for example, control one or more hardware or software components that are connected to the AP 1610 by executing an OS or an application program and may perform processing or a computation of various types of data. The AP 1610 may be implemented, for example, as a System on Chip (SoC). According to an embodiment of the present disclosure, the AP 1610 may further include a Graphics Processing Unit (GPU) and/or an image signal processor. The AP 1610 may include at least a part (for example, a cellular module 1621) of the components illustrated in FIG. 16. The AP 1610 may load a command or data received from at least one other component (for example, a non-volatile memory), process the loaded command or data, and store various types of data in the non-volatile memory.

The communication module 1620 may include the cellular module 1621, a Wireless Fidelity (WiFi) module 1623, a Bluetooth (BT) module 1625, a GPS module 1627, a Near Field Communication (NFC) module 1628, and a Radio Frequency (RF) module 1629.

The cellular module 1621 may provide services such as voice call, video call, Short Message Service (SMS), or Internet access through a communication network. According to an embodiment of the present disclosure, the cellular module 1621 may identify and authenticate the electronic device 1601 within a communication network, using the SIM card 1624. According to an embodiment of the present disclosure, the cellular module 1621 may perform at least a part of the functions of the AP 1610. According to an embodiment of the present disclosure, the cellular module 1621 may include a Communication Processor (CP).

Each of the WiFi module 1623, the BT module 1625, the GPS module 1627, and the NFC module 1628 may include, for example, a processor that may process data received or transmitted by the respective modules. According to an embodiment of the present disclosure, at least a part (for example, two or more) of the cellular module 1621, the WiFi module 1623, the BT module 1625, the GPS module 1627, and the NFC module 1628 may be included in an IC or an IC package.

The RF module 1629 may transmit and receive communication signals (for example, RF signals). The RF module 1629 may include, for example, a transceiver, a Power Amplifier Module (PAM), a frequency filter, a Low Noise Amplifier (LNA), an antenna, or the like. According to another embodiment of the present disclosure, at least one of the cellular module 1621, the WiFi module 1623, the BT module 1625, the GPS module 1627, or the NFC module 1628 may transmit and receive RF signals via a separate RF module.

The SIM card 1624 may include, for example, a card including a SIM and/or an embedded SIM. The SIM card 1624 may include a unique identifier (for example, an Integrated Circuit Card IDentifier (ICCID)) or subscriber information (for example, an International Mobile Subscriber Identity (IMSI)).

The memory 1630 (for example, the memory 130 of FIG. 1) may include, for example, an internal memory 1632 or an external memory 1634. The internal memory 1632 may be at least one of, for example, a volatile memory (for example, a Dynamic RANI (DRAM), a Static RAM (SRAM), or a Synchronous Dynamic RAM (SDRAM)), a non-volatile memory (for example, a One Time Programmable ROM (OTPROM), a Programmable ROM (PROM), an Erasable and Programmable ROM (EPROM), an Electrically Erasable and Programmable ROM (EEPROM), a mask ROM, a flash ROM, a NAND flash memory, or a NOR flash memory), a hard drive, or a Solid State Drive (SSD).

The external memory 1634 may further include, for example, a flash drive such as a Compact Flash (CF) drive, a Secure Digital (SD) memory card, a micro SD (micro-SD) memory card, a mini SD (mini-SD) memory card, an extreme Digital (xD) memory card, or a memory stick. The external memory 1634 may be operatively and/or physically coupled to the electronic device 1601 via various interfaces.

The sensor module 1640 may, for example, measure physical quantities or detect operational states associated with the electronic device 1601, and convert the measured or detected information into electrical signals. The sensor module 1640 may include at least one of, for example, a gesture sensor 1640A, a gyro sensor 1640B, a pressure sensor 1640C, a magnetic sensor 1640D, an accelerometer 1640E, a grip sensor 1640F, a proximity sensor 1640G, a color sensor (for example, a Red, Green, Blue (RGB) sensor) 1640H, a biometric sensor 16401, a temperature/humidity sensor 1640J, an illumination sensor 1640K, or an Ultra Violet (UV) light sensor 1640M. Additionally or alternatively, the sensor module 1640 may include, for example, an Electronic-nose (E-nose) sensor, an ElectroMyoGraphy (EMG) sensor, an ElectroEncephaloGram (EEG) sensor, an ElectroCardioGram (ECG) sensor, an InfraRed (IR) sensor, an iris sensor, and/or a finger print sensor. The sensor module 1640 may further include a control circuit for controlling one or more sensors included therein. According to an embodiment of the present disclosure, the electronic device 1601 may further include a processor configured to control the sensor module 1640, as a part of or separately from the AP 1610. Thus, while the AP 1610 is in a reduced power state (e.g. a sleep state), the control circuit may control the sensor module 1640.

The input device 1650 may include a touch panel 1652, a (digital) pen sensor 1654, a key 1656, or an ultrasonic input device 1658. The touch panel 1652 may operate in at least one of, for example, a capacitive, a resistive, an infrared, and an ultrasonic method. The touch panel 1652 may further include a control circuit. The touch panel 1652 may further include a tactile layer to thereby provide haptic feedback to the user.

The (digital) pen sensor 1654 may include, for example, a detection sheet which is a part of the touch panel or separately configured from the touch panel. The key 1656 may include, for example, a physical button, an optical key, or a keypad. The ultrasonic input device 1658 may be a device configured to identify data by detecting, using a microphone 1688, ultrasonic signals generated by an input tool capable of generating an ultrasonic signal.

The display 1660 may include a panel 1662, a hologram device 1664, or a projector 1666. The panel 1662 may be configured to be, for example, flexible, transparent, or wearable. The panel 1662 and the touch panel 1652 may be implemented as a single module. The hologram device 1664 may utilize the interference of light waves to provide a three-dimensional image in space. The projector 1666 may provide an image by projecting light on a screen. The screen may be positioned, for example, internally or externally to the electronic device 1601. According to an embodiment of the present disclosure, the display 1660 may further include a control circuit for controlling the panel 1662, the hologram device 1664, or the projector 1666.

The interface 1670 may include, for example, a High-Definition Multimedia Interface (HDMI) 1672, a USB 1674, an optical interface 1676, or a D-subminiature (D-sub) connector 1678. Additionally or alternatively, the interface 1670 may include, for example, a Mobile High-definition Link (MHL) interface, an SD/MultiMedia Card interface, or an Infrared Data Association (IrDA) interface.

The audio module 1680 may encode/decode a voice into an electrical signal, and vice versa. The audio module 1680 may process audio information input into, or output from, for example, a speaker 1682, a receiver 1684, an earphone 1686, or the microphone 1688.

The camera module 1691 may capture, for example, still images or a video. According to an embodiment of the present disclosure, the camera module 1691 may include one or more image sensors (for example, a front sensor or a rear sensor), a lens, an Image Signal Processor (ISP), or a flash (for example, a Light Emitting Diode (LED) or a Xenon lamp).

The power management module 1695 may manage power of the electronic device 1601. According to an embodiment of the present disclosure, the power management module 1695 may include a Power Management Integrated Circuit (PMIC), a charger IC, or a battery gauge. The PMIC may adopt wired and/or wireless charging. Wireless charging may be performed, for example, in a magnetic resonance scheme, a magnetic induction scheme, or an electromagnetic wave scheme, and may use additional circuits for wireless charging, such as a coil loop, a resonance circuit, or a rectifier. The battery gauge may measure, for example, a charge level, a voltage while charging, a current, or a temperature of the battery 1696. The battery 1696 may include, for example, a rechargeable battery and/or a solar battery.

The indicator 1697 may indicate one or more states (for example, boot status, message status, or charge status) of the electronic device 1601 or a part of the electronic device 1601 (for example, the AP 1610). The motor 1698 may convert an electrical signal into a mechanical vibration and generate vibrations or a haptic effect. The electronic device 1601 may include a device for supporting mobile TV (for example, a GPU). The device for supporting mobile TV may process media data compliant with, for example, Digital Multimedia Broadcasting (DMB), Digital Video Broadcasting (DVB), or MediaFLO.

Each of the components of the electronic device 1601 described above according to the present disclosure may include one or more components, and each component's name may vary according to the type of the electronic device. The electronic device 1601 according to an embodiment of the present disclosure may include at least one of the above-described components, and some may be omitted or additional components may be included. Also, some of the components of the electronic device 1601 according to an embodiment of the present disclosure may be combined into a single entity and perform functions identical to those of the respective components before their combination.

Figure 17:
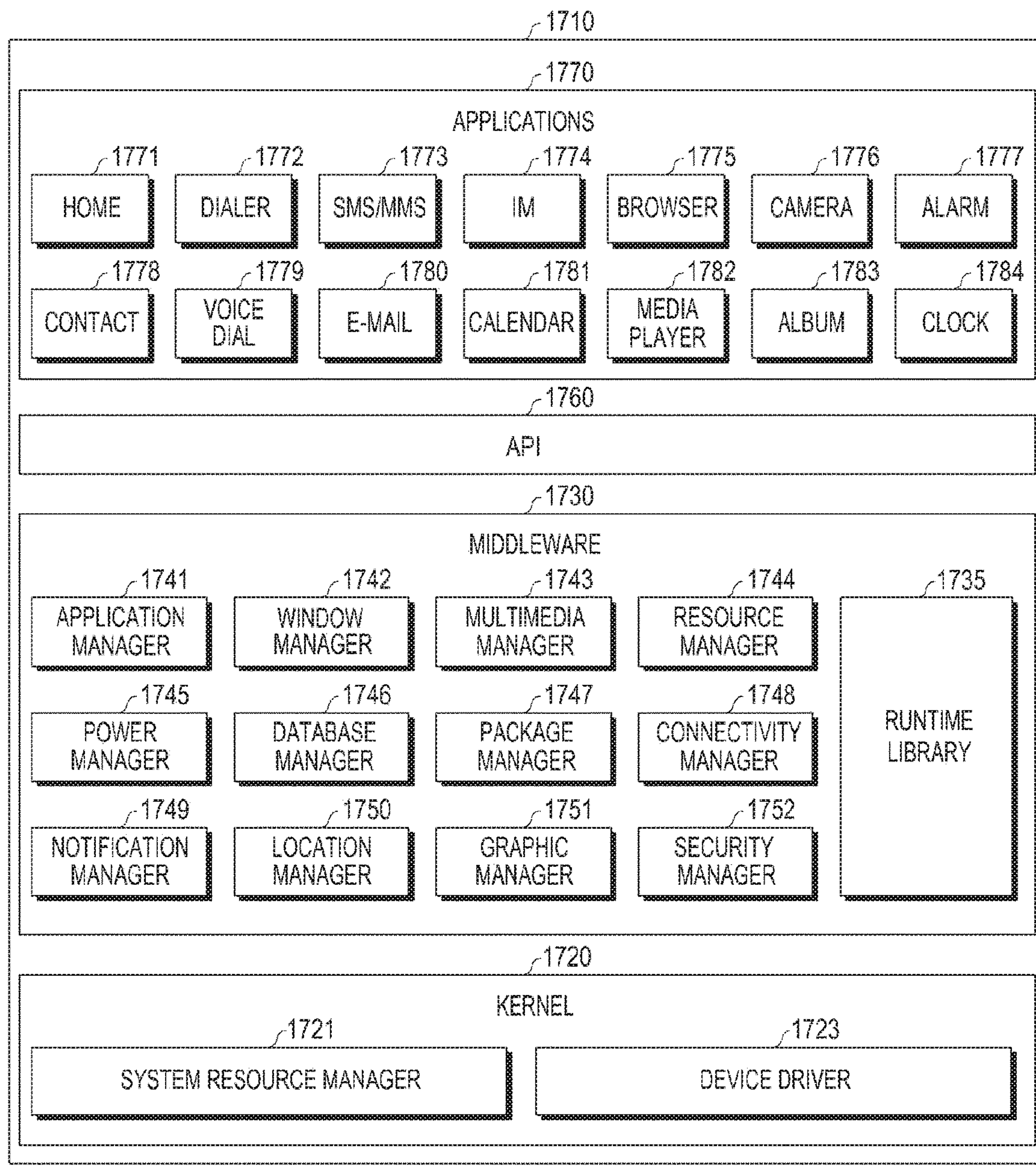
FIG. 17 is a block diagram of a programming module according to an embodiment of the present disclosure.

FIG. 17 is a block diagram of a programming module 1710 according to an embodiment of the present disclosure. According to an embodiment of the present disclosure, the programming module 1710 may include an OS that controls resources related to an electronic device and/or various applications executed on the OS (for example, application programs). For example, the OS may be Android, iOS, Windows®, Symbian, Tizen™, Bada, or the like.

Referring to FIG. 17, the programming module 1710 may include a kernel 1720, middleware 1730, an Application Programming Interface (API) 1760, and/or applications 1770. At least part of the programming module 1710 may be preloaded on an electronic device or downloaded from a server.

The kernel 1720 may include, for example, a system resource manager 1721 or a device driver 1723. The system resource manager 1721 may control, allocate, or deallocate system resources. According to an embodiment of the present disclosure, the system resource manager 1721 may include a processor manager, a memory manager, or a file system manager. The device driver 1723 may include, for example, a display driver, a camera driver, a BT driver, a shared memory driver, a USB driver, a keypad driver, a WiFi driver, an audio driver, or an Inter-Process Communication (IPC) driver.

The middleware 1730 may, for example, provide a function required commonly for the applications 1770 or provide various functions to the applications 1770 through the API 1760 so that the applications 1770 may efficiently use limited system resources available within the electronic device. According to an embodiment of the present disclosure, the middleware 1730 may include at least one of a runtime library 1735, an application manager 1741, a window manager 1742, a multimedia manager 1743, a resource manager 1744, a power manager 1745, a database manager 1746, a package manager 1747, a connectivity manager 1748, a notification manager 1749, a location manager 1750, a graphic manager 1751, or a security manager 1752.

The runtime library 1735 may include, for example, a library module that a compiler uses to add a new function in a programming language during execution of applications 1770. The runtime library 1735 may perform input/output management, memory management, a function related to an arithmetic function, or the like.

The application manager 1741 may manage, for example, a life cycle of at least one of the applications 1770. The window manager 1742 may manage Graphical User Interface (GUI) resources used by a screen. The multimedia manager 1743 may determine formats required to play various media files and may encode or decode a media file using a COder/DECoder (CODEC) suitable for the format of the media file. The resource manager 1744 may manage resources such as source code of at least one of the applications 1770, a memory, or a storage space.

The power manager 1745 may, for example, manage a battery or a power source by operating in conjunction with a Basic Input/Output System (BIOS) and may provide power information required for an operation. The database manager 1746 may manage a database for at least one of the applications 1770 so that the database may be generated, searched, or modified. The package manager 1747 may manage installation or update of an application distributed as a package file.

The connectivity manager 1748 may manage, for example, wireless connectivity of WiFi, BT, or the like. The notification manager 1749 may indicate or notify an event such as message arrival, a schedule, a proximity alarm, or the like in a manner that does not bother a user. The location manager 1750 may manage position information about the electronic device. The graphic manager 1751 may manage graphical effects to be provided to the user or related user interfaces. The security manager 1752 may provide an overall security function required for system security, user authentication, and the like. In an embodiment of the present disclosure, if the electronic device (for example, the electronic device illustrated in FIG. 8) has a telephony function, the middleware 1730 may further include a telephony manager to manage a voice or video call function of the electronic device.

Another middleware module may be created and used by combining various functions of the above-described component modules in the middleware 1730. The middleware 1730 may provide a customized module for each OS type in order to provide differentiated functions. In addition, the middleware 1730 may dynamically delete a part of the existing components or add a new component.

The API 1760 is, for example, a set of API programming functions, which may be configured differently according to an OS. For example, in the case of Android or iOS, one API set may be provided per platform, whereas in the case of Tizen™, two or more API sets may be provided per platform.

The applications 1770 may include, for example, one or more applications capable of providing functions such as a home 1771, a dialer 1772, a Short Message Service/Multimedia Messaging Service (SMS/MMS) 1773, an Instant Message (IM) 1774, a browser 1775, a camera 1776, an alarm 1777, contacts 1778, voice dial 1779, email 1780, a calendar 1781, a media player 1782, an album 1783, or a clock 1784, health care (for example, measurement of an exercise amount or a glucose level), or providing environmental information (for example, information about air pressure, humidity, or temperature).

According to an embodiment of the present disclosure, the applications 1770 may include an application supporting information exchange between the electronic device (for example, the electronic devices illustrated in FIG. 1, 2, 3, 7, 9, 12, or 14) and an external electronic device (for the convenience of description, referred to as an "information exchange application"). The information exchange application may include, for example, a notification relay application for transmitting certain information to an external electronic device or a device management application for managing an external electronic device.

For example, the notification relay application may include a function of transmitting notification information generated from another application (for example, an SMS/MMS application, an email application, a health care application, or an environmental information application) to the external electronic device. Also, the notification relay application may, for example, receive notification information from an external electronic device and transmit the received notification information to a user. The device management application may, for example, manage (for example, install, delete, or update) at least a part of the functions of an external electronic device communicating with the electronic device 101 (for example, turn-on/turn-off of the external electronic device (or a part of its components) or control of the brightness (or resolution) of the display), an application executed in the external electronic device, or a service (for example, a call service or a message service) provided by the external electronic device.

According to an embodiment of the present disclosure, the applications 1770 may include an application (for example, a health care application) designated according to a property (for example, the type of the electronic device as a property of the electronic device is a mobile medical device) of the external electronic device. According to an embodiment of the present disclosure, the applications 1770 may include an application received from an external electronic device. The applications 1770 may include a preloaded application or a third party application downloadable from a server. The names of components of the programming module 1710 according to an embodiment of the present disclosure may vary according to the type of OS.

According to an embodiment of the present disclosure, at least a part of the programming module 1710 may be implemented in software, firmware, hardware, or in a combination of at least two of them. At least a part of the programming module 1710 may be implemented (for example, executed) by the processor (for example, an AP 3310). At least a part of the programming module 1710 may include, for example, a module, a program, a routine, a set of instructions, or a process to execute one or more functions.

The terms "module" and "function" as used herein may include their ordinary meanings including, for example, a unit of one, or a combination of two or more. The terms "module" and "function" may be used interchangeably with terms such as, for example, "unit," "logic," "logical block," "component" or "circuit." The terms "module" and "function" may refer to the smallest unit for performing one or more functions, or a portion thereof. The terms "module" and "function" may refer to an entity implemented mechanically, or electronically. For example, the terms "module" and "function" may include at least one of a known, or to-be-developed, Application-Specific Integrated Circuit (ASIC), Field-Programmable Gate Array (FPGA) or programmable logic device that performs certain operations.

At least a part of devices (for example, modules and their functions) or methods according to an embodiment of the present disclosure may be implemented as commands stored in a non-transitory computer-readable storage medium, in the form of a programming module. When commands are executed by a processor (for example, the controller 210,

310, 710, 910, 1210, or 1410), one or more processors may execute functions corresponding to the commands. The non-transitory computer-readable storage medium may be, for example, the memory 130 of FIG. 1.

The non-transitory computer-readable storage medium may include a hard disk, a floppy disk, a tape, a magnetic media (for example, a magnetic tape), an optical media (for example, a Compact Disc Read-Only Memory (CD-ROM)), a DVD, a magneto-optical media (for example, a floptical disk), hardware devices (for example, a ROM, a RAM or a flash memory)), and the like. Program instructions may include machine language code that is generated by a compiler or high-level language code that may be executed by a computer using an interpreter. The functions of hardware discussed above may be implemented as one or more software modules, and vice versa in order to perform an operation according to an embodiment of the present disclosure.

A module or a programming module according to an embodiment of the present disclosure may include one or more of the above-described components, may omit a portion thereof, or may include additional components. Operations that are performed by a module, a programming module or other components according to the present disclosure may be processed in a serial, parallel, repetitive or heuristic manner, and some operations may be omitted or additional operations may be added.

According to an embodiment of the present disclosure, a storage medium storing commands is provided. The commands are configured to allow at least one processor to perform at least one operation, when the commands are executed by the at least one processor. The at least one operation may include determining whether an external device has been connected to an external device connector including at least one contact exposed externally from a housing of the electronic device and electrically connected to an external electronic device, sensing a temperature by a temperature sensor connected to the at least one contact of the external device connector, and determining the temperature sensed by the temperature sensor to be a skin temperature, if it is determined that the external electronic device has not been connected to the external device connector.

Figure 18:
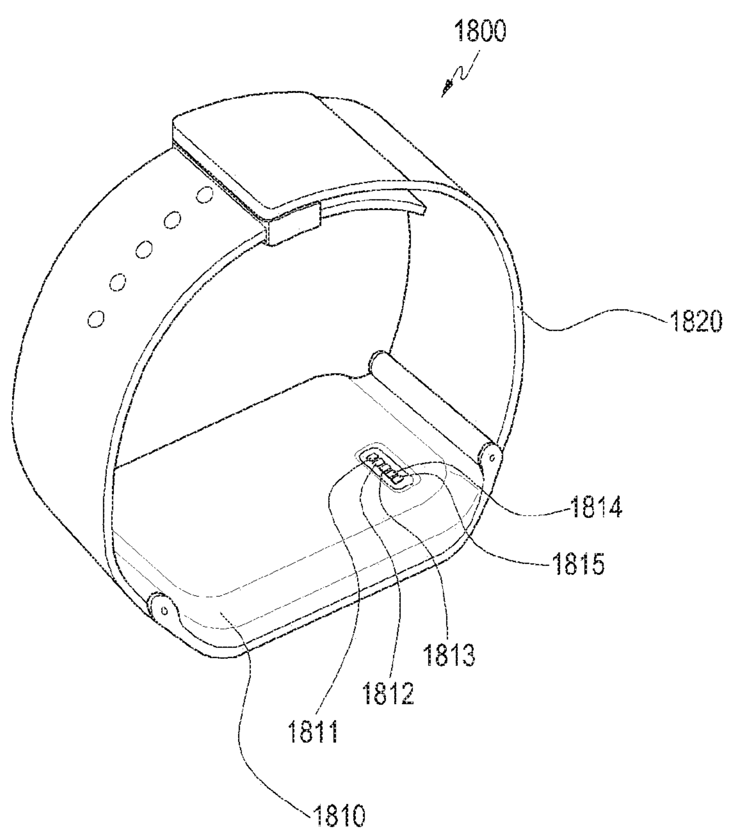
FIG. 18 illustrates a wearable device according to an embodiment of the present disclosure.

FIG. 18 illustrates a wearable device 1800 according to an embodiment of the present disclosure.

Referring to FIG. 18, the wearable device 1800 according to an embodiment of the present disclosure may include a housing 1810 or a coupling member 1820. While the wearable device 1800 is shown in FIG. 18 as including the housing 1810 and the coupling member 1820, the housing 1810 and the coupling member 1820 may be integrated into one unit, or the wearable device 1810 may be configured to be wearable without the coupling member 1820.

According to an embodiment of the present disclosure, at least one contact 1811, 1812, 1813, 1814, and 1815 may be included in the housing 1810 or the coupling member 1820. For example, when a user wears the wearable device 1800, the at least one contact 1811, 1812, 1813, 1814, and 1815 may contact the skin of the user.

According to an embodiment of the present disclosure, when the at least one contact 1811, 1812, 1813, 1814, and 1815 contacts the skin of a user, heat transferred from the skin of the user may be provided to a temperature sensor of the wearable device 1800 through the at least one contact 1811, 1812, 1813, 1814, and 1815. The temperature sensor may sense skin temperature by measuring received heat.

As is apparent from the foregoing description, according to the electronic device and the method for determining a temperature in the electronic device according to an embodiment of the present disclosure, the electronic device (for example, a wearable device) can accurately measure skin temperature through an external device connector (for example, a Pogo pin) without using a separate structure (for example, an electrode provided at a part contacting the skin of a user) for temperature sensing. Since the structure of the electronic device is simplified, material cost can be reduced and the electronic device is advantageous in design or part installation.

In addition, the electronic device and the method for determining a temperature in the electronic device according to an embodiment of the present disclosure can be readily applied to a small-size wearable device.

According to the electronic device and the method for determining a temperature in the electronic device according to an embodiment of the present disclosure, since the skin temperature of a human body is constantly measured through a temperature sensor installed in a wearable device, an ovulation period of a woman can be analyzed and utilized, and the skin temperature can be used for the purpose of fitness or Internet of Things (IoT) in daily life or during sleep.

Further, the electronic device and the method for determining a temperature in the electronic device according to an embodiment of the present disclosure can find their applications in various fields using a reliable skin temperature measurement. In addition, various and accurate services can be provided in conjunction with other sensors in the electronic device.

While the present disclosure has been shown and described with reference to certain embodiments thereof, it will be understood by those skilled in the art that various changes in form and details may be made therein without departing from the scope and spirit of the disclosure as defined by the appended claims and their equivalents.

What is claimed is:

1. An electronic device detachable from and attachable to a user, the electronic device comprising: a battery; a conductive member exposed to an external area of the electronic device; a temperature sensor electrically connected to the conductive member; and a circuit electrically connected to the battery, the conductive member; and the temperature sensor, wherein the circuit comprises: at least one processor; a first part of the circuit electrically connected to the battery; and a second part of the circuit electrically connected to the temperature sensor and the first part of the circuit, wherein the at least one processor is configured to: when value of a current or a voltage received through the conductive member is less than a specified reference value, identify a skin temperature of a user in contact with the conductive member using the temperature sensor; and when a value of a current or a voltage received through the conductive member is equal to or larger than the specified reference value, control the first part of the circuit to supply power received from an external device connected to the conductive member to the battery, and identify a temperature of the battery using the temperature sensor.

2. The electronic device of claim 1, wherein the temperature sensor is disposed on a first surface of a circuit board including the circuit, wherein the conductive member is disposed on a second surface of the circuit board, and wherein the second surface is opposite to the first surface and faces a direction in which the conductive member is exposed to the external area of the electronic device.

3. The electronic device of claim 1, further comprising another temperature sensor to sense an ambient temperature of the electronic device, wherein the circuit is further configured to correct the skin temperature sensed by the temperature sensor based on the ambient temperature of the electronic device.

4. The electronic device of claim 1, wherein the conductive member is an antenna radiator.

* * * * *